US006475231B2

(12) United States Patent
Dobak, III et al.

(10) Patent No.: US 6,475,231 B2
(45) Date of Patent: Nov. 5, 2002

(54) METHOD AND DEVICE FOR APPLICATIONS OF SELECTIVE ORGAN COOLING

(75) Inventors: John D. Dobak, III, La Jolla, CA (US);
Juan C. Lasheras, La Jolla, CA (US);
Randell L. Werneth, San Diego, CA (US)

(73) Assignee: Innercool Therapies, Inc., San Diego, CA (US)

( * ) Notice: Subject to any disclaimer, the term of this patent is extended or adjusted under 35 U.S.C. 154(b) by 0 days.

(21) Appl. No.: 09/755,919

(22) Filed: Jan. 5, 2001

(65) Prior Publication Data

US 2001/0001831 A1 May 24, 2001

Related U.S. Application Data

(60) Division of application No. 09/215,040, filed on Dec. 16, 1998, now Pat. No. 6,251,130, which is a continuation-in-part of application No. 09/103,342, filed on Jun. 23, 1998, now Pat. No. 6,096,068, and a continuation-in-part of application No. 09/052,545, filed on Mar. 31, 1998, now Pat. No. 6,231,595, and a continuation-in-part of application No. 09/047,012, filed on Mar. 24, 1998, now Pat. No. 5,957,963, and a continuation-in-part of application No. 09/215,038, filed on Dec. 16, 1998, now Pat. No. 6,261,312, and a continuation-in-part of application No. 09/215,039, filed on Dec. 16, 1998, now Pat. No. 6,251,129.

(51) Int. Cl.[7] .................................................. A61F 7/00
(52) U.S. Cl. ........................ 607/105; 607/106; 607/113; 128/898
(58) Field of Search ........................ 607/96, 104, 105, 607/106, 113; 128/898; 606/191, 192, 194, 198

(56) References Cited

U.S. PATENT DOCUMENTS 2,308,484 A   1/1943   Auzin et al.
2,374,609 A   4/1945   McCollum (List continued on next page.)

FOREIGN PATENT DOCUMENTS

EP   0655225 A1   5/1993

(List continued on next page.)

OTHER PUBLICATIONS

Ambrus; *The Biphasic Nature and Temperature Dependence of the Activation of Human Plasminogen by Urokinase;* May 1979; pp. 339–347; Research Communications in Chemical Pathology and Pharmacology, vol. 24, No. 2.

(List continued on next page.)

*Primary Examiner*—Rosiland S. Kearney
(74) *Attorney, Agent, or Firm*—Mark D. Wieczorek

(57) ABSTRACT

The invention provides a method and device for selectively controlling the temperature of a selected organ of a patient for performance of a specified application. The method includes introducing a guide catheter into a blood vessel. The guide catheter may have a soft tip and a retaining flange, and may be used to provide treatments such as administration of thrombolytic drug therapies, stenting procedures, angiographic procedures, etc. A supply tube is provided having a heat transfer element attached to a distal end thereof. The heat transfer element having a plurality of exterior surface irregularities, these surface irregularities having a depth greater than the boundary layer thickness of flow in the feeding artery of the selected organ. The supply tube and heat transfer element may be inserted through the guide catheter to place the heat transfer element in the feeding artery of the selected organ. Turbulence is created around the surface irregularities at a distance from the heat transfer element greater than the boundary layer thickness of flow in the feeding artery, thereby creating turbulence throughout the blood flow in the feeding artery. A working fluid is circulated into the heat transfer element via the supply tube and via an internal lumen of the heat transfer element. The fluid may be circulated out of the heat transfer element via an external lumen of the heat transfer element and through the guide catheter. Heat is thereby transferred between the heat transfer element and the blood in the feeding artery to selectively control the temperature of the selected organ during or soon before or after the specified application.

6 Claims, 12 Drawing Sheets

U.S. PATENT DOCUMENTS

| | | |
|---|---|---|
| 2,615,686 A | 10/1952 | Davidson |
| 2,672,032 A | 3/1954 | Towse |
| 2,913,009 A | 11/1959 | Kuthe |
| 3,298,371 A | 1/1967 | Lee |
| 3,425,419 A | 2/1969 | Dato |
| 3,504,674 A | 4/1970 | Swenson et al. |
| 3,612,175 A | 10/1971 | Ford et al. |
| 3,865,116 A | 2/1975 | Brooks |
| 3,888,259 A | 6/1975 | Miley |
| 3,971,383 A | 7/1976 | Van Gerven |
| 4,038,519 A | 7/1977 | Foucras |
| 4,153,048 A | 5/1979 | Magrini |
| 4,190,033 A | 2/1980 | Foti |
| 4,231,425 A | 11/1980 | Engstrom |
| 4,275,734 A | 6/1981 | Mitchiner |
| 4,298,006 A | 11/1981 | Parks |
| 4,318,722 A | 3/1982 | Altman |
| 4,323,071 A * | 4/1982 | Simpson et al. ...... 128/DIG. 18 |
| 4,427,009 A | 1/1984 | Wells et al. |
| 4,445,500 A | 5/1984 | Osterholm |
| 4,483,341 A | 11/1984 | Witteles |
| 4,502,286 A | 3/1985 | Okada et al. |
| 4,569,355 A | 2/1986 | Bitterly |
| 4,581,017 A | 4/1986 | Sahota |
| 4,602,642 A | 7/1986 | O'Hara |
| 4,655,746 A | 4/1987 | Daniels et al. |
| 4,672,962 A | 6/1987 | Hershenson |
| 4,745,922 A | 5/1988 | Taylor |
| 4,748,979 A | 6/1988 | Hershenson |
| 4,750,493 A | 6/1988 | Brader |
| 4,762,130 A | 8/1988 | Fogarty et al. |
| 4,860,744 A | 8/1989 | Johnson et al. |
| 4,883,455 A | 11/1989 | Leonard |
| 4,894,164 A | 1/1990 | Polaschegg |
| 4,904,237 A | 2/1990 | Janese |
| 4,920,963 A | 5/1990 | Brader |
| 4,951,677 A | 8/1990 | Crowley et al. |
| 4,964,409 A | 10/1990 | Tremulis |
| 5,000,734 A | 3/1991 | Boussignac |
| 5,002,531 A | 3/1991 | Bonzel |
| 5,014,695 A | 5/1991 | Benak et al. |
| 5,018,521 A | 5/1991 | Campbell |
| 5,019,075 A | 5/1991 | Spears et al. |
| 5,024,668 A | 6/1991 | Peters et al. |
| 5,041,089 A | 8/1991 | Mueller et al. |
| 5,046,497 A | 9/1991 | Millar |
| 5,078,713 A | 1/1992 | Varney |
| 5,089,260 A | 2/1992 | Hunter et al. |
| 5,092,841 A | 3/1992 | Spears |
| 5,106,360 A | 4/1992 | Ishwara et al. |
| 5,108,390 A | 4/1992 | Potocky et al. |
| RE33,911 E | 5/1992 | Samson et al. |
| 5,110,721 A | 5/1992 | Anaise et al. |
| 5,117,822 A | 6/1992 | Laghi |
| 5,147,355 A | 9/1992 | Friedman et al. |
| 5,149,321 A | 9/1992 | Klatz et al. |
| 5,150,706 A | 9/1992 | Cox et al. |
| 5,151,100 A | 9/1992 | Abele et al. |
| 5,190,539 A | 3/1993 | Fletcher et al. |
| 5,191,883 A | 3/1993 | Lennox et al. |
| 5,196,024 A | 3/1993 | Barath |
| 5,211,631 A | 5/1993 | Sheaff |
| 5,234,405 A | 8/1993 | Klatz et al. |
| 5,246,421 A | 9/1993 | Saab |
| 5,248,312 A | 9/1993 | Langberg |
| 5,250,070 A | 10/1993 | Parodi |
| 5,257,977 A | 11/1993 | Eshel |
| 5,264,260 A | 11/1993 | Saab |
| 5,267,341 A | 11/1993 | Shearin |
| 5,269,369 A | 12/1993 | Faghri |
| 5,269,749 A | 12/1993 | Koturov |
| 5,269,758 A | 12/1993 | Taheri |
| 5,281,213 A | 1/1994 | Milder et al. |
| 5,281,215 A | 1/1994 | Milder |
| 5,306,261 A | 4/1994 | Alliger et al. |
| 5,310,440 A | 5/1994 | Zingher |
| 5,322,518 A | 6/1994 | Schneider et al. |
| 5,330,435 A | 6/1994 | Vaillancourt |
| 5,334,193 A | 8/1994 | Nardella |
| 5,342,301 A | 8/1994 | Saab |
| 5,342,621 A | 8/1994 | Eury |
| 5,344,436 A | 9/1994 | Fontenot et al. |
| 5,358,486 A | 10/1994 | Saab |
| 5,365,750 A | 11/1994 | Greenthal |
| 5,368,591 A | 11/1994 | Lennox et al. |
| 5,383,854 A | 1/1995 | Safer et al. |
| 5,383,918 A | 1/1995 | Panetta |
| 5,395,314 A | 3/1995 | Klatz et al. |
| 5,395,331 A | 3/1995 | O'Neill et al. |
| 5,403,281 A | 4/1995 | O'Neill et al. |
| 5,417,686 A | 5/1995 | Peterson et al. |
| 5,423,745 A | 6/1995 | Todd et al. |
| 5,423,807 A | 6/1995 | Milder |
| 5,433,740 A | 7/1995 | Yamaguchi |
| 5,437,673 A | 8/1995 | Baust et al. |
| 5,443,456 A | 8/1995 | Alliger et al. |
| 5,462,521 A | 10/1995 | Brucker et al. |
| 5,486,204 A | 1/1996 | Clifton |
| 5,486,208 A | 1/1996 | Ginsburg |
| 5,496,271 A | 3/1996 | Burton et al. |
| 5,499,973 A | 3/1996 | Saab |
| 5,531,776 A | 7/1996 | Ward et al. |
| 5,549,559 A | 8/1996 | Eshel |
| 5,558,644 A | 9/1996 | Boyd et al. |
| 5,569,195 A | 10/1996 | Saab |
| 5,573,532 A | 11/1996 | Chang et al. |
| 5,578,008 A | 11/1996 | Hara |
| 5,584,804 A | 12/1996 | Klatz et al. |
| 5,588,438 A | 12/1996 | McKown et al. |
| 5,591,162 A | 1/1997 | Fletcher et al. |
| 5,620,480 A | 4/1997 | Rudie |
| 5,622,182 A | 4/1997 | Jaffe |
| 5,624,392 A | 4/1997 | Saab |
| 5,630,837 A | 5/1997 | Crowley |
| 5,643,197 A | 7/1997 | Brucker et al. |
| 5,647,051 A | 7/1997 | Neer |
| 5,653,692 A | 8/1997 | Masterson et al. |
| 5,676,693 A | 10/1997 | Lafontaine |
| 5,709,654 A | 1/1998 | Katz |
| 5,713,941 A | 2/1998 | Robins et al. |
| 5,716,386 A | 2/1998 | Ward et al. |
| 5,733,318 A | 3/1998 | Augustine |
| 5,735,809 A | 4/1998 | Gorsuch |
| 5,797,878 A | 8/1998 | Bleam |
| 5,799,661 A | 9/1998 | Boyd et al. |
| 5,800,480 A | 9/1998 | Augustine et al. |
| 5,800,483 A | 9/1998 | Vought |
| 5,800,516 A * | 9/1998 | Fine et al. ................... 128/898 |
| 5,807,391 A | 9/1998 | Wijkamp |
| 5,820,593 A | 10/1998 | Safer et al. |
| 5,824,030 A | 10/1998 | Yang et al. |
| 5,827,222 A | 10/1998 | Klatz et al. |
| 5,827,237 A | 10/1998 | Macoviak et al. |
| 5,827,269 A | 10/1998 | Saadat |
| 5,833,671 A | 11/1998 | Macoviak et al. |
| 5,837,003 A | 11/1998 | Ginsburg |
| 5,861,021 A | 1/1999 | Thome et al. |
| 5,871,526 A | 2/1999 | Gibbs et al. |
| 5,873,835 A | 2/1999 | Hastings et al. |
| 5,879,316 A | 3/1999 | Safer et al. |
| 5,879,329 A | 3/1999 | Ginsburg |

| | | |
|---|---|---|
| 5,899,898 A | 5/1999 | Arless et al. |
| 5,899,899 A | 5/1999 | Arless et al. |
| 5,902,268 A | 5/1999 | Saab |
| 5,906,588 A | 5/1999 | Safer et al. |
| 5,906,594 A | 5/1999 | Scarfone et al. |
| 5,906,636 A | 5/1999 | Casscells, III et al. |
| 5,913,856 A | 6/1999 | Chia et al. |
| 5,913,885 A | 6/1999 | Klatz et al. |
| 5,913,886 A | 6/1999 | Soloman |
| 5,916,242 A | 6/1999 | Schwartz |
| 5,957,963 A | 9/1999 | Dobak, III |
| 5,971,979 A | 10/1999 | Joye et al. |
| 5,989,238 A | 11/1999 | Ginsburg |
| 6,019,783 A | 2/2000 | Philips et al. |
| 6,022,336 A | 2/2000 | Zadno-Azizi et al. |
| 6,024,740 A | 2/2000 | Lesh et al. |
| 6,033,383 A | 3/2000 | Ginsburg |
| 6,042,559 A | 3/2000 | Dobak, III |
| 6,051,019 A | 4/2000 | Dobak, III |
| 6,096,068 A | 8/2000 | Dobak, III |
| 6,110,168 A | 8/2000 | Ginsburg |
| 6,126,684 A | 10/2000 | Gobin et al. |
| 6,146,411 A | 11/2000 | Noda et al. |
| 6,149,670 A | 11/2000 | Worthen et al. |
| 6,149,673 A | 11/2000 | Ginsburg |
| 6,149,676 A | 11/2000 | Ginsburg |
| 6,149,677 A | 11/2000 | Dobak, III |
| 6,165,207 A | 12/2000 | Balding et al. |
| 6,224,624 B1 | 5/2001 | Lasheras et al. |
| 6,231,594 B1 | 5/2001 | Dae |
| 6,231,595 B1 | 5/2001 | Dobak, III |
| 6,235,048 B1 | 5/2001 | Dobak, III |
| 6,238,428 B1 | 5/2001 | Werneth et al. |
| 6,245,095 B1 | 6/2001 | Dobak, III et al. |
| 6,251,129 B1 | 6/2001 | Dobak, III et al. |
| 6,251,130 B1 | 6/2001 | Dobak, III et al. |
| 6,254,626 B1 | 7/2001 | Dobak, III et al. |
| 6,261,312 B1 | 7/2001 | Dobak, III et al. |
| 6,264,679 B1 | 7/2001 | Keller et al. |
| 6,287,326 B1 | 9/2001 | Pecor |
| 6,290,697 B1 | 9/2001 | Tu et al. |
| 6,291,717 B1 | 9/2001 | Takai et al. |
| 6,299,599 B1 | 10/2001 | Pham et al. |
| 6,306,161 B1 | 10/2001 | Ginsburg |
| 6,312,452 B1 | 11/2001 | Dobak, III et al. |
| 6,325,818 B1 | 12/2001 | Werneth |
| 6,338,727 B1 | 1/2002 | Noda et al. |
| 6,354,099 B1 | 3/2002 | Bieberich |
| 2001/0001830 A1 | 5/2001 | Dobak, III et al. |
| 2001/0001831 A1 | 5/2001 | Dobak, III et al. |
| 2001/0001832 A1 | 5/2001 | Dobak, III et al. |
| 2001/0002442 A1 | 5/2001 | Dobak, III |
| 2001/0005791 A1 | 6/2001 | Ginsburg et al. |
| 2001/0007951 A1 | 7/2001 | Dobak, III |
| 2001/0008975 A1 | 7/2001 | Dobak, III et al. |
| 2001/0010011 A1 | 7/2001 | Aliberto et al. |
| 2001/0011184 A1 | 8/2001 | Dobak, III et al. |
| 2001/0011185 A1 | 8/2001 | Dobak, III et al. |
| 2001/0016763 A1 | 8/2001 | Lasheras et al. |
| 2001/0016764 A1 | 8/2001 | Dobak, III |
| 2001/0021865 A1 | 9/2001 | Dobak, III et al. |
| 2001/0021866 A1 | 9/2001 | Dobak, III et al. |
| 2001/0029394 A1 | 10/2001 | Dobak, III et al. |
| 2001/0032004 A1 | 10/2001 | Werneth |
| 2001/0039440 A1 | 11/2001 | Lasheras et al. |
| 2001/0041923 A1 | 11/2001 | Dobak, III |
| 2001/0044644 A1 | 11/2001 | Keller et al. |
| 2001/0047191 A1 | 11/2001 | Lasersohn et al. |
| 2001/0047192 A1 | 11/2001 | Lasersohn et al. |
| 2001/0047196 A1 | 11/2001 | Ginsburg et al. |
| 2001/0049545 A1 | 12/2001 | Lasersohn et al. |
| 2002/0016621 A1 | 2/2002 | Werneth et al. |
| 2002/0022871 A1 | 2/2002 | Grahn et al. |
| 2002/0026227 A1 | 2/2002 | Philips |
| 2002/0029016 A1 | 3/2002 | Pham et al. |
| 2002/0032474 A1 | 3/2002 | Dobak, III et al. |

FOREIGN PATENT DOCUMENTS

| | | |
|---|---|---|
| EP | 0 664 990 | 11/1997 |
| FR | 2 447 406 | 3/1980 |
| SU | 806 029 | 2/1981 |
| WO | WO 91/05528 | 5/1991 |
| WO | WO 93/04727 | 3/1993 |
| WO | WO 95/01814 | 1/1995 |
| WO | WO 96/40347 | 12/1996 |
| WO | WO 97/01374 | 1/1997 |
| WO | WO 97/25011 | 7/1997 |
| WO | WO 97/32518 | 9/1997 |
| WO | WO 98/26831 | 6/1998 |
| WO | WO 98/31312 | 7/1998 |
| WO | WO 98/49957 | 11/1998 |
| WO | WO 99/02096 | 1/1999 |
| WO | WO 99/37226 | 7/1999 |
| WO | WO 99/44519 | 9/1999 |
| WO | WO 99/48449 | 9/1999 |
| WO | WO 99/56812 | 11/1999 |
| WO | WO 99/66970 | 12/1999 |
| WO | WO 99/66971 | 12/1999 |
| WO | WO 00/09054 | 2/2000 |
| WO | WO 00/10494 | 3/2000 |
| WO | WO 00/38601 | 7/2000 |
| WO | WO 00/47145 | 8/2000 |
| WO | WO 00/48670 | 8/2000 |
| WO | WO 00/51534 | 9/2000 |
| WO | WO 00/53135 | 9/2000 |
| WO | WO 00/57823 | 10/2000 |
| WO | WO 00/62837 | 10/2000 |
| WO | WO 00/66053 | 11/2000 |
| WO | WO 00/72779 | 12/2000 |
| WO | WO 00/72787 | 12/2000 |
| WO | WO 01/03606 | 1/2001 |
| WO | WO 01/08580 | 2/2001 |
| WO | WO 01/10323 | 2/2001 |
| WO | WO 01/10365 | 2/2001 |
| WO | WO 01/12061 | 2/2001 |
| WO | WO 01/12122 | 2/2001 |
| WO | WO 01/13809 | 3/2001 |
| WO | WO 01/13837 | 3/2001 |
| WO | WO 01/17471 | 3/2001 |
| WO | WO 01/19447 | 3/2001 |
| WO | WO 01/26590 | 4/2001 |
| WO | WO 01/30413 | 5/2001 |
| WO | WO 01/41708 | 6/2001 |
| WO | WO 01/43661 | 6/2001 |
| WO | WO 01/49236 | 7/2001 |
| WO | WO 01/52781 | 7/2001 |
| WO | WO 01/56517 | 8/2001 |
| WO | WO 01/58397 | 8/2001 |
| WO | WO 01/64145 | 9/2001 |
| WO | WO 01/64146 | 9/2001 |
| WO | WO 01/66052 | 9/2001 |
| WO | WO 01/74276 | 10/2001 |
| WO | WO 01/76655 | 10/2001 |
| WO | WO 01/78580 | 10/2001 |
| WO | WO 01/87379 | 11/2001 |
| WO | WO 01/95840 | 12/2001 |

OTHER PUBLICATIONS

Bigelo; *Hypothermia, Its Possible Role in Cardiac Surgery;* Nov. 1959; pp. 849–866; Annals of Surgery, vol. 132, No. 5.

Cheatle; *Cryostripping the Long and Short Saphenous Veins;* Jan. 1993; one page; Br. J. Surg., vol. 80.

Dexter; *Blood Warms as It Blows Retrograde from a Femoral Cannulation Site to the Carotid Artery During Cardiopulmonary Bypass;* Nov. 1994; pp. 393–397; Perfusion, vol. 9, No. 6.

Gillinov; *Superior Cerebral Protection with Profound Hypothermia During Circulatory Arrest;* Nov. 1992; pp. 1432–1439; Ann. Thorac. Surg., vol. 55.

Higazi; *The Effect of Ultrasonic Irradiation and Temperature on Fibrinolytic Activity in Vitro;* Aug. 1992; p. 251–253; Thrombosis Research, vol. 69, No. 2.

Imamaki; *Retrograde Cerebral Perfusion with Hypothermic Blood Provides Efficient Protection of the Brain;* Jul. 1995; pp. 325–333; Journal of Cardiac Surgery, vol. 10, No. 4, Part 1.

Jolin; *Management of a Giant Intracranial Aneurysm Using Surface–Heparinized Extracorporeal Circulation and Controlled Deep Hypothermic Low Flow Perfusion;* Aug. 1992; pp. 756–760; Acta Anaesthesiologica Scandinavia.

Jos R.C. Jansen, Ph.D., et al., (1997) *Near continuous cardiac output by thermodilution.* Journal of Clinical Monitoring 13:233–239.

Kimoto; *Open Heart Surgery under Direct Vision with the Aid of Brain–Cooling by Irragation;* Jul. 1955; pp. 592–603; Surgery, vol. 39, No. 4.

Marekovic, Z.; *Abstract of Renal Hypothermia in Situ by Venous Passages: Experimental Work on Dogs;* 1980; Eur Urol 6(2); 1 page.

Meden; *Effect of Hypothermia and Delayed Thrombolysis in a Rat Embolic Stroke Model;* Dec. 1993; pp. 91–98; Acta Neurologica Scandinavica.

Meden; *The Influence of Body Temperature on Infarct Volume and Thrombolytic Therapy in a Rat Embolic Stroke Model;* Feb. 1994; pp. 131–138; Brain Research, vol. 647.

Milleret, Rene; *La cryo–chirurgie danes les varices des mimbres inferieurs;* Angiologie; Supplement au No. 110.

Milleret; Abstract of *Cryosclerosis of the Saphenous Veins in Varicose Reflux in the Obese and Elderly;* 10.1981; one page; Phlebologie, vol. 34, No. 4.

Parkins; *Brain Cooling in the Prevention of Brain Damage During Periods of Circulatory Occlusion in Dogs;* Apr. 1954; pp. 284–289; Annals of Surgery; vol. 140, No. 3.

Piepgras; *Rapid Active Internal Core Cooling for Induction of Moderate Hypothermia in Head Injury by Use of an Extracorporeal Heat Exchanger,* Feb. 1998; pp. 311–318; Neurosurgery, vol. 42, No. 2.

Rijken; *Plasminogen Activation at Low Temperatures in Plasma Samples Containing Therapeutic Concentrations of Tissue–Type Plasminogen Activator or Other Thrombolytic Agents;* Oct. 1989; pp. 47–521 place of publication unknown.

Schwartz, A.E. et al.; (1996); *Isolated cerebral hypothermia by single carotid artery perfusion of extracorporeally cooled blood in baboons;* Neurosurgery 39(3):577–582.

Schwartz; *Cerebral Blood Flow during Low–flow Hypothermic Cardiopulmonary Bypass in Baboons;* Jun. 1994; pp. 959–964; Anesthesiology, vol. 81, No. 4.

Schwartz; *Selective Cerebral Hypothermia by Means of Transfemoral Internal Carotid Artery Catheterization;* May 1996; pp. 571–572; Radiology, vol. 201, No. 2.

Steen; *The Detrimental Effects of Prolonged Hypothermia and Rewarming in the Dog;* Aug. 1979 ;pp. 224–230; Anesthesiology, vol. 52, No. 3.

Vandam; *Hypothermia;* Sep. 1959; pp. 546–553; The New England Journal of Medicine.

White; *Cerebral Hypothermia and Circulatory Arrest;* Jul. 1978; pp. 450–458; Mayo Clinic Proceedings, vol. 53.

Yenari; *Thrombolysis with Tissue Plasminogen Activator (TPA) is Temperature Dependent;* Jul. 1994; pp. 475–481; Thrombosis Research, vol. 77, No. 5.

Yoshihara; *Changes in Coagulation and Fibrinolysis Occuring in Dogs during Hypothermia;* Aug. 1984; pp. 503–512; Thrombosis Research, vol. 37, No. 4.

Zarins; *Circulation in Profound Hypothermia;* Nov. 1972; pp. 97–104; Journal of Surgical Research, vol. 14, N. 2.

Maas, C.; "Intermittent Antegrade Selective Cerebral Perfusion During Circulatory Arrest for Repair of Aortic Arch"; Perfusion, vol. 12, No. 2, pp. 127–132 (1997).

Colvett, K.; "Opportunities with Combined Modality Therapy for Selective Organ Preservation in Muscle–Invasive Bladder Cancer."; Journal of Surgical Oncology, vol. 63, No. 3, pp. 201–208, (1996).

Shiraki, et al.; "Esophageal and Tympanic Temperature Responses to Core Blood Temperature Changes During Hyperthermia"; the American Physiological Society; 1986; pp. 98–102.

Capogna, G., et al.; "I.V. Clonidine for Post–Extradural Shivering in Parturients: A Preliminary Study"; British Journal of Anaesthesia; 1993; 71: 294–295.

Alfonsi, Pascal, et al.; "The Effects of Meperidine and Sufentanil on the Shivering Threshold in Postoperative Patients"; Anesthesiology; V. 89, No. 1, Jul. 1998; pp. 43–48.

* cited by examiner

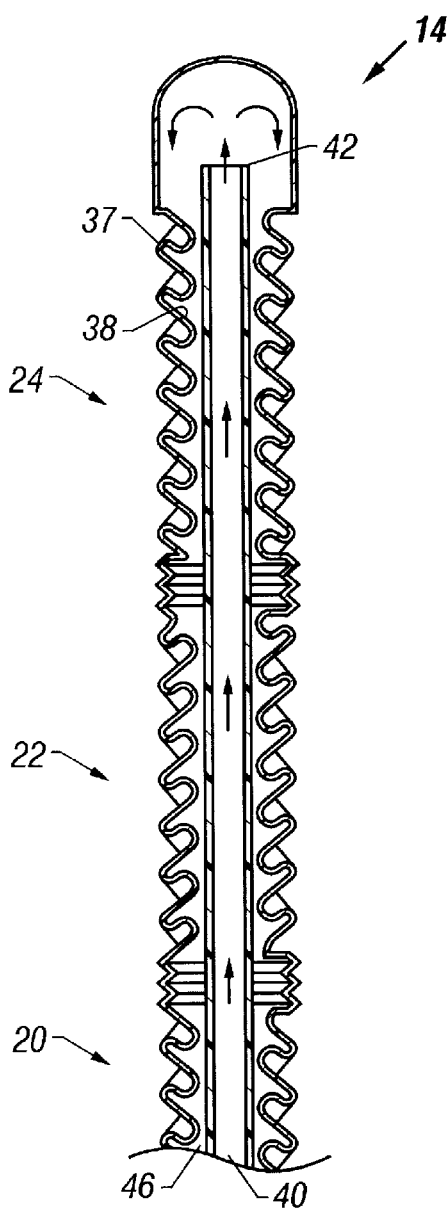
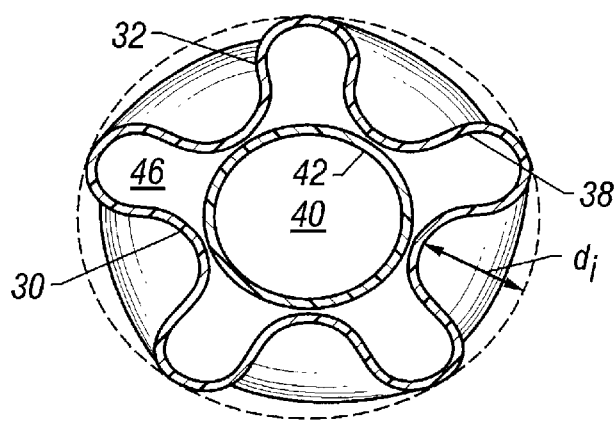
FIG. 3
FIG. 4

METHOD AND DEVICE FOR APPLICATIONS OF SELECTIVE ORGAN COOLING

CROSS REFERENCE TO RELATED APPLICATIONS

This is a divisional patent application of co-pending U.S. patent application Ser. No. 09/215,040 filed on Dec. 16, 1998, U.S. Pat. No. 6,251,130 and entitled "Method and Device for Applications of Selective Organ Cooling" which is a continuation-in-part patent application of co-pending U.S. patent applications: Ser. No. 09/103,342, filed on Jun. 23, 1998, U.S. Pat. No. 6,096,068 and entitled "Selective Organ Cooling Catheter and Method of Using the Same"; Ser. No. 09/052,545, filed on Mar. 31, 1998, U.S. Pat. No. 6,231,545 and entitled "Circulating Fluid Hypothermia Method and Apparatus"; Ser. No. 09/047,012, filed on Mar. 24, 1998, and entitled "Improved Selective Organ Hypothermia Method and Apparatus", now U.S. Pat. No. 5,957,963 issued on Sep. 28, 1999; Ser. No. 09/215,038, filed on Dec. 16, 1998, U.S. Pat. No. 6,261,312 and entitled "An Inflatable Catheter for Selective Organ Heating and Cooling and Method of Using the Same"; and Ser. No. 09/215,039, filed on Dec. 16, 1998, U.S. Pat. No. 6,251,129 and entitled "Method for Low Temperature Thrombolysis and Low Temperature Thrombolytic Agent with Selective Organ Control"; the entirety of each being incorporated by reference herein.

BACKGROUND OF THE INVENTION

1. Field of the Invention

The present invention relates generally to the modification and control of the temperature of a selected body organ. More particularly, the invention relates to applications of selective organ cooling which advantageously employ complementary techniques.

2. Background Information

Organs in the human body, such as the brain, kidney and heart, are maintained at a constant temperature of approximately 37° C. Hypothermia can be clinically defined as a core body temperature of 35° C. or less. Hypothermia is sometimes characterized further according to its severity. A body core temperature in the range of 33° C. to 35° C. is described as mild hypothermia. A body temperature of 28° C. to 32° C. is described as moderate hypothermia. A body core temperature in the range of 24° C. to 28° C. is described as severe hypothermia.

Hypothermia is uniquely effective in reducing brain injury caused by a variety of neurological insults and may eventually play an important role in emergency brain resuscitation. Experimental evidence has demonstrated that cerebral cooling improves outcome after global ischemia, focal ischemia, or traumatic brain injury. For this reason, hypothermia may be induced in order to reduce the effect of certain bodily injuries to the brain as well as other organs.

Cerebral hypothermia has traditionally been accomplished through whole body cooling to create a condition of total body hypothermia in the range of 20° C. to 30° C. However, the use of total body hypothermia risks certain deleterious systematic vascular effects. For example, total body hypothermia may cause severe derangement of the cardiovascular system, including low cardiac output, elevated systematic resistance, and ventricular fibrillation. Other side effects include renal failure, disseminated intravascular coagulation, and electrolyte disturbances. In addition to the undesirable side effects, total body hypothermia is difficult to administer.

Catheters have been developed which are inserted into the bloodstream of the patient in order to induce total body hypothermia. For example, U.S. Pat. No. 3,425,419 to Dato describes a method and apparatus of lowering and raising the temperature of the human body. Dato induces moderate hypothermia in a patient using a metallic catheter. The metallic catheter has an inner passageway through which a fluid, such as water, can be circulated. The catheter is inserted through the femoral vein and then through the inferior vena cava as far as the right atrium and the superior vena cava. The Dato catheter has an elongated cylindrical shape and is constructed from stainless steel. By way of example, Dato suggests the use of a catheter approximately 70 cm in length and approximately 6 mm in diameter. However, use of the Dato device implicates the negative effects of total body hypothermia described above.

Due to the problems associated with total body hypothermia, attempts have been made to provide more selective cooling. For example, cooling helmets or head gear have been used in an attempt to cool only the head rather than the patient's entire body. However, such methods rely on conductive heat transfer through the skull and into the brain. One drawback of using conductive heat transfer is that the process of reducing the temperature of the brain is prolonged. Also, it is difficult to precisely control the temperature of the brain when using conduction due to the temperature gradient that must be established externally in order to sufficiently lower the internal temperature. In addition, when using conduction to cool the brain, the face of the patient is also subjected to severe hypothermia, increasing discomfort and the likelihood of negative side effects. It is known that profound cooling of the face can cause similar cardiovascular side effects as total body cooling. From a practical standpoint, such devices are cumbersome and may make continued treatment of the patient difficult or impossible.

Selected organ hypothermia has been accomplished using extracorporeal perfusion, as detailed by Arthur E. Schwartz, M.D. et al., in *Isolated Cerebral Hypothermia by Single Carotid Artery Perfusion of Extracorporeally Cooled Blood in Baboons,* which appeared in Vol. 39, No. 3, NEUROSURGERY 577 (September, 1996). In this study, blood was continually withdrawn from baboons through the femoral artery. The blood was cooled by a water bath and then infused through a common carotid artery with its external branches occluded. Using this method, normal heart rhythm, systemic arterial blood pressure and arterial blood gas values were maintained during the hypothermia. This study showed that the brain could be selectively cooled to temperatures of 20° C. without reducing the temperature of the entire body. However, external circulation of blood is not a practical approach for treating humans because the risk of infection, need for anticoagulation, and risk of bleeding is too great. Further, this method requires cannulation of two vessels making it more cumbersome to perform particularly in emergency settings. Even more, percutaneous cannulation of the carotid artery is difficult and potentially fatal due to the associated arterial wall trauma. Finally, this method would be ineffective to cool other organs, such as the kidneys, because the feeding arteries cannot be directly cannulated percutaneously.

Selected organ hypothermia has also been attempted by perfusion of a cold solution such as saline or perflourocarbons. This process is commonly used to protect the heart during heart surgery and is referred to as cardioplegia.

Perfusion of a cold solution has a number of drawbacks, including a limited time of administration due to excessive volume accumulation, cost, and inconvenience of maintaining the perfusate and lack of effectiveness due to the temperature dilution from the blood. Temperature dilution by the blood is a particular problem in high blood flow organs such as the brain.

BRIEF SUMMARY OF THE INVENTION

The invention provides a practical method and apparatus which modifies and controls the temperature of a selected organ and which may be used in combination with many complementary therapeutic techniques.

In one aspect, the invention is directed to a method for selectively controlling the temperature of a selected organ of a patient for performance of a specified application. The method includes introducing a guide catheter into a blood vessel and providing a supply tube having a heat transfer element attached to a distal end thereof. The heat transfer element has a plurality of exterior surface irregularities, the surface irregularities having a depth greater than the boundary layer thickness of flow in the feeding artery of the selected organ. The supply tube and heat transfer element are inserted through the guide catheter to place the heat transfer element in the feeding artery of the selected organ. Turbulence is created around the surface irregularities at a distance from the heat transfer element greater than the boundary layer thickness of flow in the feeding artery, thereby creating turbulence throughout the blood flow in the feeding artery. A working fluid is circulated into the heat transfer element via the supply tube. The working fluid is circulated out of the heat transfer element via the guide catheter. Heat is thereby transferred between the heat transfer element and the blood in the feeding artery to selectively control the temperature of the selected organ.

Implementations of the invention may include one or more of the following. The surface irregularities on the heat transfer element may include a plurality of segments of helical ridges and grooves having alternating directions of helical rotation. Turbulence may be created by establishing repetitively alternating directions of helical blood flow with the alternating helical rotations of the ridges and grooves, and may be induced for greater than 20% of the period of the cardiac cycle within the carotid artery.

In another aspect, the invention relates to a method for selective thrombolysis by selective vessel hypothermia. The method includes introducing a guide catheter into a thrombosed blood vessel, delivering a thrombolytic drug to the blood by flowing the thrombolytic drug into the guide catheter, and introducing a supply tube having a heat transfer element at a distal end thereof into the thrombosed blood vessel through the guide catheter. The heat transfer element is cooled by flowing a working fluid through the heat transfer element, the return path for the working fluid being the guide catheter. The blood is thereby cooled to a prespecified temperature by flowing the blood past the heat transfer element. The system may also be used to heat the blood for hyperthermia applications.

Implementations of the invention may include one or more of the following. The drug may be chosen from the group consisting of tPA, urokinase, streptokinase, precursors of urokinase, and combinations thereof. For hypothermia applications, if the thrombolytic drug is streptokinase, the prespecified temperature range may be between about 30° C. and 32° C. If the thrombolytic drug is urokinase or a precursor to urokinase, the prespecified temperature range may be below about 28° C. For hyperthermia applications, if the thrombolytic drug is tPA, the prespecified temperature range may be between about 37° C. to 40° C.

In another aspect, the invention is directed to a selective organ heat transfer device and guide catheter assembly. The assembly includes a guide catheter capable of insertion to a selected feeding artery in the vascular system of a patient, the guide catheter having a soft tip and an interior retaining flange at a distal end. The assembly also includes a flexible supply tube capable of insertion in the guide catheter and a heat transfer element attached to a distal end of the supply tube. The heat transfer element has a flange at a distal end, the flange capable of engagement with the retaining flange to prevent the heat transfer element from disengaging with the guide catheter. A plurality of exterior surface irregularities are disposed on the heat transfer element, the surface irregularities being shaped and arranged to create turbulence in surrounding fluid, the surface irregularities having a depth at least equal to the boundary layer thickness of flow in the feeding artery.

Implementations of the invention include one or more of the following. A strut may be coupled to the supply tube at a distal end thereof. The heat transfer element may include a plurality of heat transfer segments, and may further include a flexible joint connecting each of the heat transfer segments to adjacent the heat transfer segments. The flexible joint may be a bellows, a metal tube, a plastic tube, a rubber tube, a latex rubber tube, etc.

In another aspect, the invention is directed to a method for performing angiography during selective vessel hypothermia. The method includes introducing a guide catheter into a blood vessel and delivering a radioopaque fluid to the blood by flowing the radioopaque fluid into the guide catheter. A supply tube having a heat transfer element at a distal end thereof is introduced into the blood vessel through the guide catheter. The heat transfer element is cooled by flowing a working fluid through the heat transfer element, the return path for the working fluid being the guide catheter. Blood is thereby cooled by flowing past the heat transfer element. Thus, the cooling can occur at or near the same time as angiography.

In another aspect, the invention is directed to a method for performing stenting of a stenotic lesion during selective vessel hypothermia. The method includes introducing a guide catheter into a blood vessel and introducing a guide wire through the guide catheter and across a stenotic lesion. A balloon catheter loaded with a stent is then delivered via the guide wire such that the stent is positioned across the lesion. The balloon is expanded with contrast, after which the stent may be deployed. The heat transfer element and supply tube may then be employed to cool the blood as described above. Similarly, the cooling can occur at or near the same time as the stenting procedure.

In another aspect of the invention, a return catheter may be coupled to a heat transfer element, distal end of the heat transfer element defining a hole. The return catheter and heat transfer element may together form a "guide catheter" through which may be placed a guide wire, a microcatheter, etc. In particular, a catheter may be placed therein having a tapered shape such that the catheter lodges into the hole. The catheter may have an outlet at a distal end to allow drug delivery, an outlet upstream of the distal end to allow delivery of a working fluid to the interior of the heat transfer element, or in some cases both.

Advantages of the invention include the following. The device may be placed in an artery without traumatizing the arterial wall and with damaging the device itself. The device may be placed in an artery simply and by a variety of practitioners such as cardiologists or neurosurgeons. The device allows the complementary performance of simultaneous procedures along with brain cooling, these procedures including angiography, stenotic lesion stenting, and drug delivery.

The novel features of this invention, as well as the invention itself, will be best understood from the attached drawings, taken along with the following description, in which similar reference characters refer to similar parts, and in which:

BRIEF DESCRIPTION OF THE SEVERAL VIEWS OF THE DRAWINGS

FIG. 3 is longitudinal section view of the heat transfer element of FIG. 2;

FIG. 4 is a transverse section view of the heat transfer element of FIG. 2;

DETAILED DESCRIPTION OF THE INVENTION

Figure 1:
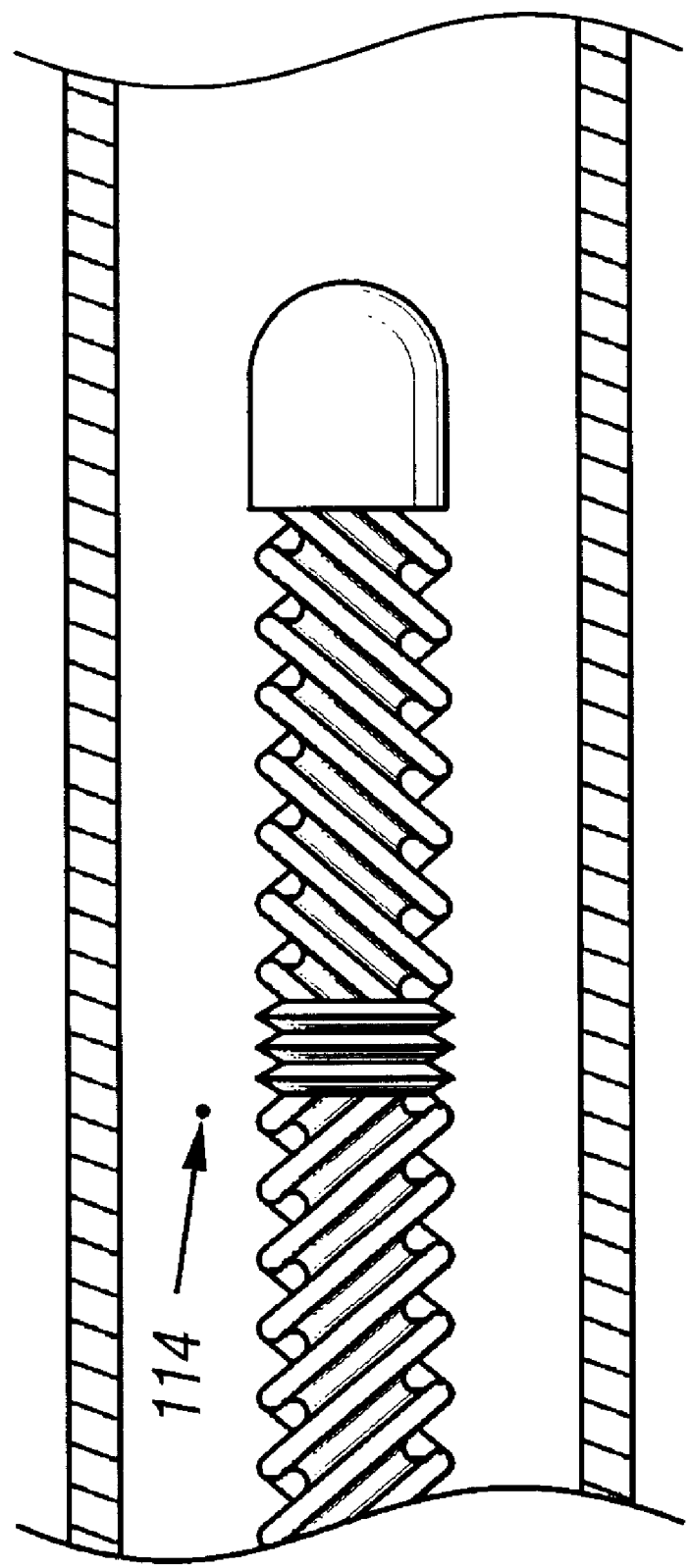
FIG. 1 is an elevation view of a turbulence inducing heat transfer element within an artery.

The temperature of a selected organ may be intravascularly regulated by a heat transfer element placed in the organ's feeding artery to absorb or deliver heat to or from the blood flowing into the organ. While the method is described with respect to blood flow into an organ, it is understood that heat transfer within a volume of tissue is analogous. In the latter case, heat transfer is predominantly by conduction.

The heat transfer may cause either a cooling or a heating of the selected organ. A heat transfer element that selectively alters the temperature of an organ should be capable of providing the necessary heat transfer rate to produce the desired cooling or heating effect within the organ to achieve a desired temperature.

The heat transfer element should be small and flexible enough to fit within the feeding artery while still allowing a sufficient blood flow to reach the organ in order to avoid ischemic organ damage. Feeding arteries, like the carotid artery, branch off the aorta at various levels. Subsidiary arteries continue to branch off these initial branches. For example, the internal carotid artery branches off the common carotid artery near the angle of the jaw. The heat transfer element is typically inserted into a peripheral artery, such as the femoral artery, using a guide catheter or guide wire, and accesses a feeding artery by initially passing though a series of one or more of these branches. Thus, the flexibility and size, e.g., the diameter, of the heat transfer element are important characteristics. This flexibility is achieved as is described in more detail below.

These points are illustrated using brain cooling as an example. The common carotid artery supplies blood to the head and brain. The internal carotid artery branches off the common carotid artery to supply blood to the anterior cerebrum. The heat transfer element may be placed into the common carotid artery or into both the common carotid artery and the internal carotid artery.

The benefits of hypothermia described above are achieved when the temperature of the blood flowing to the brain is reduced to between 30° C. and 32° C. A typical brain has a blood flow rate through each carotid artery (right and left) of approximately 250–375 cubic centimeters per minute (cc/min). With this flow rate, calculations show that the heat transfer element should absorb approximately 75–175 watts of heat when placed in one of the carotid arteries to induce the desired cooling effect. Smaller organs may have less blood flow in their respective supply arteries and may require less heat transfer, such as about 25 watts.

The method employs conductive and convective heat transfers. Once the materials for the device and a working fluid are chosen, the conductive heat transfers are solely dependent on the temperature gradients. Convective heat transfers, by contrast, also rely on the movement of fluid to transfer heat. Forced convection results when the heat transfer surface is in contact with a fluid whose motion is induced (or forced) by a pressure gradient, area variation, or other such force. In the case of arterial flow, the beating heart provides an oscillatory pressure gradient to force the motion of the blood in contact with the heat transfer surface. One of the aspects of the device uses turbulence to enhance this forced convective heat transfer.

The rate of convective heat transfer Q is proportional to the product of S, the area of the heat transfer element in direct contact with the fluid, $\Delta T = T_b - T_s$, the temperature differential between the surface temperature $T_s$ of the heat transfer element and the free stream blood temperature $T_b$, and $\overline{h}_c$, the average convection heat transfer coefficient over the heat transfer area. $\overline{h}_c$ is sometimes called the "surface coefficient of heat transfer" or the "convection heat transfer coefficient".

The magnitude of the heat transfer rate Q to or from the fluid flow can be increased through manipulation of the above three parameters. Practical constraints limit the value of these parameters and how much they can be manipulated. For example, the internal diameter of the common carotid artery ranges from 6 to 8 mm. Thus, the heat transfer element residing therein may not be much larger than 4 mm in diameter to avoid occluding the vessel. The length of the heat transfer element should also be limited. For placement within the internal and common carotid artery, the length of the heat transfer element is limited to about 10 cm. This estimate is based on the length of the common carotid artery, which ranges from 8 to 12 cm.

Consequently, the value of the surface area S is limited by the physical constraints imposed by the size of the artery into which the device is placed. Surface features, such as fins, can be used to increase the surface area of the heat transfer element, however, these features alone cannot provide enough surface area enhancement to meet the required heat transfer rate to effectively cool the brain.

One may also attempt to vary the magnitude of the heat transfer rate by varying $\Delta T$. The value of $\Delta T = T_b - T_s$ can be varied by varying the surface temperature $T_s$ of the heat transfer element. The allowable surface temperature of the heat transfer element is limited by the characteristics of blood. The blood temperature is fixed at about 37° C., and blood freezes at approximately 0° C. When the blood approaches freezing, ice emboli may form in the blood which may lodge downstream, causing serious ischemic injury. Furthermore, reducing the temperature of the blood also increases its viscosity which results in a small decrease in the value of $\overline{h_c}$. Increased viscosity of the blood may further result in an increase in the pressure drop within the artery, thus compromising the flow of blood to the brain. Given the above constraints, it is advantageous to limit the surface temperature of the heat transfer element to approximately 1° C.–5° C., thus resulting in a maximum temperature differential between the blood stream and the heat transfer element of approximately 32° C.–36° C.

One may also attempt to vary the magnitude of the heat transfer rate by varying $\overline{h_c}$. Fewer constraints are imposed on the value of the convection heat transfer coefficient $\overline{h_c}$. The mechanisms by which the value of $\overline{h_c}$ may be increased are complex. However, one way to increase $\overline{h_c}$ for a fixed mean value of the velocity is to increase the level of turbulent kinetic energy in the fluid flow.

The heat transfer rate $Q_{no-flow}$ in the absence of fluid flow is proportional to $\Delta T$, the temperature differential between the surface temperature $T_s$ of the heat transfer element and the free stream blood temperature $T_b$ times k, the diffusion constant, and is inversely proportion to $\delta$, the thickness of the boundary layer.

The magnitude of the enhancement in heat transfer by fluid flow can be estimated by taking the ratio of the heat transfer rate with fluid flow to the heat transfer rate in the absence of fluid flow $N = Q_{flow}/Q_{no-flow} = \overline{h_c}/(k/\delta)$. This ratio is called the Nusselt number ("Nu"). For convective heat transfer between blood and the surface of the heat transfer element, Nusselt numbers of 30–80 have been found to be appropriate for selective cooling applications of various organs in the human body. Nusselt numbers are generally dependent on several other numbers: the Reynolds number, the Womersley number, and the Prandtl number.

Stirring-type mechanisms, which abruptly change the direction of velocity vectors, may be utilized to induce turbulent kinetic energy and increase the heat transfer rate. The level of turbulence so created is characterized by the turbulence intensity $\theta$. Turbulence intensity $\theta$ is defined as the root mean square of the fluctuating velocity divided by the mean velocity. Such mechanisms can create high levels of turbulence intensity in the free stream, thereby increasing the heat transfer rate. This turbulence intensity should ideally be sustained for a significant portion of the cardiac cycle, and should ideally be created throughout the free stream and not just in the boundary layer.

Turbulence does occur for a short period in the cardiac cycle anyway. In particular, the blood flow is turbulent during a small portion of the descending systolic flow. This portion is less than 20% of the period of the cardiac cycle. If a heat transfer element is placed co-axially inside the artery, the heat transfer rate will be enhanced during this short interval. For typical of these fluctuations, the turbulence intensity is at least 0.05. In other words, the instantaneous velocity fluctuations deviate from the mean velocity by at least 5%. Although ideally turbulence is created throughout the entire period of the cardiac cycle, the benefits of turbulence are obtained if the turbulence is sustained for 75%, 50% or even as low as 30% or 20% of the cardiac cycle.

One type of turbulence-inducing heat transfer element which may be advantageously employed to provide heating or cooling of an organ or volume is described in co-pending U.S. patent application Ser. No. 09/103,342 to Dobak and Lasheras for a "Selective Organ Cooling Catheter and Method of Using the Same," incorporated by reference above. In that application, and as described below, the heat transfer element is made of a high thermal conductivity material, such as metal. The use of a highly thermally conductive material increases the heat transfer rate for a given temperature differential between the coolant within the heat transfer element and the blood. This facilitates the use of a higher temperature coolant within the heat transfer element, allowing safer coolants, such as water, to be used. Highly thermally conductive materials, such as metals, tend to be rigid. In that application, bellows provided a high degree of articulation that compensated for the intrinsic stiffness of the metal. In an application incorporated by reference above, the bellows are replaced with a straight metal tube having a predetermined thickness to allow flexibility via bending of the metal. Alternatively, the bellows may be replaced with a polymer tube, e.g., a latex rubber tube, a plastic tube, or a flexible plastic corrugated tube.

The device size may be minimized, e.g., less than 4 mm, to prevent blockage of the blood flowing in the artery. The design of the heat transfer element should facilitate flexibility in an inherently inflexible material.

To create the desired level of turbulence intensity in the blood free stream during the whole cardiac cycle, one embodiment of the device uses a modular design. This design creates helical blood flow and produces a high level of turbulence in the free stream by periodically forcing abrupt changes in the direction of the helical blood flow. FIG. 1 is a perspective view of such a turbulence inducing heat transfer element within an artery. Turbulent flow would be found at point 114, in the free stream area. The abrupt changes in flow direction are achieved through the use of a series of two or more heat transfer segments, each comprised of one or more helical ridges. To affect the free stream, the depth of the helical ridge is larger than the thickness of the boundary layer which would develop if the heat transfer element had a smooth cylindrical surface.

The use of periodic abrupt changes in the helical direction of the blood flow in order to induce strong free stream turbulence may be illustrated with reference to a common clothes washing machine. The rotor of a washing machine spins initially in one direction causing laminar flow. When the rotor abruptly reverses direction, significant turbulent kinetic energy is created within the entire wash basin as the changing currents cause random turbulent motion within the clothes-water slurry.

Figure 2:
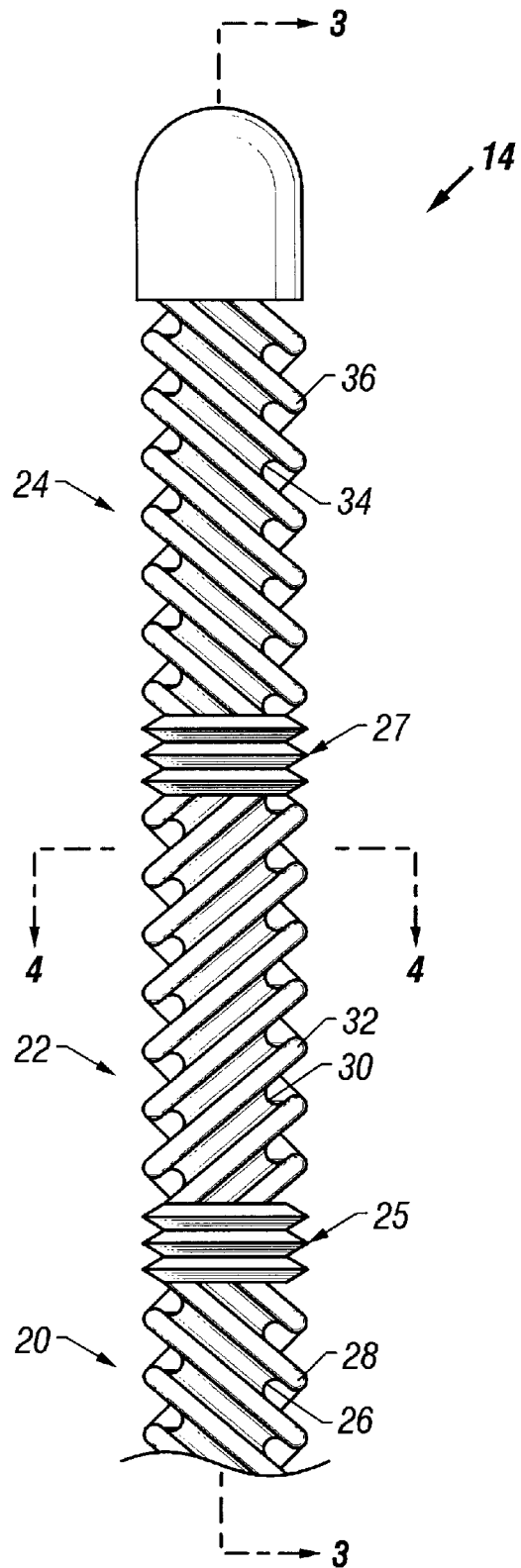
FIG. 2 is an elevation view of one embodiment of a heat transfer element which may be employed according to the invention.

FIG. 2 is an elevation view of one embodiment of a heat transfer element 14. The heat transfer element 14 is comprised of a series of elongated, articulated segments or modules 20, 22, 24. Three such segments are shown in this embodiment, but two or more such segments could be used. As seen in FIG. 2, a first elongated heat transfer segment 20 is located at the proximal end of the heat transfer element 14. A turbulence-inducing exterior surface of the segment 20 comprises four parallel helical ridges 28 with four parallel helical grooves 26 therebetween. One, two, three, or more parallel helical ridges 28 could also be used. In this embodiment, the helical ridges 28 and the helical grooves 26 of the heat transfer segment 20 have a left hand twist, referred to herein as a counter-clockwise spiral or helical rotation, as they proceed toward the distal end of the heat transfer segment 20.

The first heat transfer segment 20 is coupled to a second elongated heat transfer segment 22 by a first tube section 25, which provides flexibility. The second heat transfer segment 22 comprises one or more helical ridges 32 with one or more helical grooves 30 therebetween. The ridges 32 and grooves 30 have a right hand, or clockwise, twist as they proceed toward the distal end of the heat transfer segment 22. The second heat transfer segment 22 is coupled to a third elongated heat transfer segment 24 by a second tube section 27. The third heat transfer segment 24 comprises one or more helical ridges 36 with one or more helical grooves 34 therebetween. The helical ridge 36 and the helical groove 34 have a left hand, or counter-clockwise, twist as they proceed toward the distal end of the heat transfer segment 24. Thus, successive heat transfer segments 20, 22, 24 of the heat transfer element 14 alternate between having clockwise and counterclockwise helical twists. The actual left or right hand twist of any particular segment is immaterial, as long as adjacent segments have opposite helical twist.

In addition, the rounded contours of the ridges 28, 32, 36 also allow the heat transfer element 14 to maintain a relatively atraumatic profile, thereby minimizing the possibility of damage to the blood vessel wall. A heat transfer element may be comprised of two, three, or more heat transfer segments.

The tube sections 25, 27 are formed from seamless and nonporous materials, such as metal, and therefore are impermeable to gas, which can be particularly important, depending on the type of working fluid which is cycled through the heat transfer element 14. The structure of the tube sections 25, 27 allows them to bend, extend and compress, which increases the flexibility of the heat transfer element 14 so that it is more readily able to navigate through blood vessels. The tube sections 25, 27 are also able to tolerate cryogenic temperatures without a loss of performance. The tube sections 25, 27 may have a predetermined thickness of their walls, such as between about 0.5 and 0.8 mils. The predetermined thickness is to a certain extent dependent on the diameter of the overall tube. Thicknesses of 0.5 to 0.8 mils may be appropriate especially for a tubal diameter of about 4 mm. For smaller diameters, such as about 3.3 mm, larger thicknesses may be employed for higher strength. In another embodiment, tube sections 25, 27 may be formed from a polymer material such as rubber, e.g., latex rubber.

The exterior surfaces of the heat transfer element 14 can be made from metal except in flexible joint embodiment where the surface may be comprised of a polymer material. The metal may be a very high thermal conductivity material such as nickel, thereby facilitating efficient heat transfer. Alternatively, other metals such as stainless steel, titanium, aluminum, silver, copper and the like, can be used, with or without an appropriate coating or treatment to enhance biocompatibility or inhibit clot formation. Suitable biocompatible coatings include, e.g., gold, platinum or polymer paralyene. The heat transfer element 14 may be manufactured by plating a thin layer of metal on a mandrel that has the appropriate pattern. In this way, the heat transfer element 14 may be manufactured inexpensively in large quantities, which is an important feature in a disposable medical device.

Because the heat transfer element 14 may dwell within the blood vessel for extended periods of time, such as 24–48 hours or even longer, it may be desirable to treat the surfaces of the heat transfer element 14 to avoid clot formation. One means by which to prevent thrombus formation is to bind an antithrombogenic agent to the surface of the heat transfer element 14. For example, heparin is known to inhibit clot formation and is also known to be useful as a biocoating. Alternatively, the surfaces of the heat transfer element 14 may be bombarded with ions such as nitrogen. Bombardment with nitrogen can harden and smooth the surface and, thus prevent adherence of clotting factors to the surface.

FIG. 3 is a longitudinal sectional view of the heat transfer element 14, taken along line 3—3 in FIG. 2. Some interior contours are omitted for purposes of clarity. An inner tube 42 creates an inner coaxial lumen 42 and an outer coaxial lumen 46 within the heat transfer element 14. Once the heat transfer element 14 is in place in the blood vessel, a working fluid such as saline or other aqueous solution may be circulated through the heat transfer element 14. Fluid flows up a supply catheter into the inner coaxial lumen 40. At the distal end of the heat transfer element 14, the working fluid exits the inner coaxial lumen 40 and enters the outer lumen 46. As the working fluid flows through the outer lumen 46, heat is transferred from the working fluid to the exterior surface 37 of the heat transfer element 14. Because the heat transfer element 14 is constructed from a high conductivity material, the temperature of its exterior surface 37 may reach very close to the temperature of the working fluid. The tube 42 may be formed as an insulating divider to thermally separate the inner lumen 40 from the outer lumen 46. For example, insulation may be achieved by creating longitudinal air channels in the wall of the insulating tube 42. Alternatively, the insulating tube 42 may be constructed of a non-thermally conductive material like polytetrafluoroethylene or some other polymer.

It is important to note that the same mechanisms that govern the heat transfer rate between the exterior surface 37 of the heat transfer element 14 and the blood also govern the heat transfer rate between the working fluid and the interior surface 38 of the heat transfer element 14. The heat transfer characteristics of the interior surface 38 are particularly important when using water, saline or other fluid which remains a liquid as the coolant. Other coolants such as freon undergo nucleate boiling and create turbulence through a different mechanism. Saline is a safe coolant because it is non-toxic, and leakage of saline does not result in a gas embolism, which could occur with the use of boiling refrigerants. Since turbulence in the coolant is enhanced by the shape of the interior surface 38 of the heat transfer element 14, the coolant can be delivered to the heat transfer element 14 at a warmer temperature and still achieve the necessary heat transfer rate.

This has a number of beneficial implications in the need for insulation along the catheter shaft length. Due to the decreased need for insulation, the catheter shaft diameter can be made smaller. The enhanced heat transfer characteristics of the interior surface of the heat transfer element 14 also allow the working fluid to be delivered to the heat transfer element 14 at lower flow rates and lower pressures. High pressures may make the heat transfer element stiff and cause it to push against the wall of the blood vessel, thereby shielding part of the exterior surface 37 of the heat transfer element 14 from the blood. Because of the increased heat transfer characteristics achieved by the alternating helical ridges 28, 32, 36, the pressure of the working fluid may be as low as 5 atmospheres, 3 atmospheres, 2 atmospheres or even less than 1 atmosphere.

FIG. 4 is a transverse sectional view of the heat transfer element 14, taken at a location denoted by the line 4—4 in FIG. 2. FIG. 4 illustrates a five-lobed embodiment, whereas FIG. 2 illustrates a four-lobed embodiment. As mentioned earlier, any number of lobes might be used. In FIG. 4, the coaxial construction of the heat transfer element 14 is clearly shown. The inner coaxial lumen 40 is defined by the insulating coaxial tube 42. The outer lumen 46 is defined by the exterior surface of the insulating coaxial tube 42 and the interior surface 38 of the heat transfer element 14. In addition, the helical ridges 32 and helical grooves 30 may be seen in FIG. 4. As noted above, in the preferred embodiment, the depth of the grooves, $d_i$, is greater than the boundary layer thickness which would have developed if a cylindrical heat transfer element were introduced. For example, in a heat transfer element 14 with a 4 mm outer diameter, the depth of the invaginations, $d_i$, may be approximately equal to 1 mm if designed for use in the carotid artery. Although FIG. 4 shows four ridges and four grooves, the number of ridges and grooves may vary. Thus, heat transfer elements with 1, 2, 3, 4, 5, 6, 7, 8 or more ridges are specifically contemplated.

Figure 5:
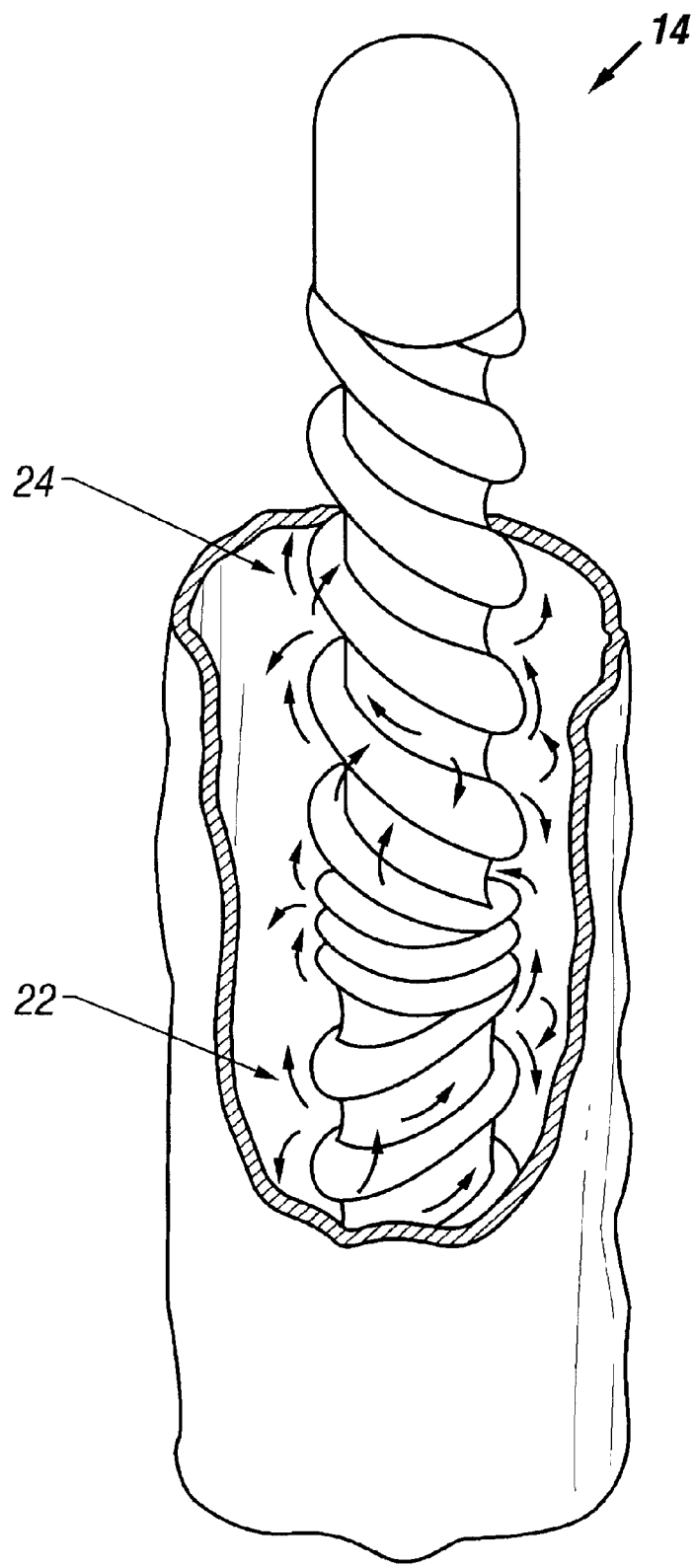
FIG. 5 is a perspective view of the heat transfer element of FIG. 2 in use within a blood vessel.

FIG. 5 is a perspective view of a heat transfer element 14 in use within a blood vessel, showing only one helical lobe per segment for purposes of clarity. Beginning from the proximal end of the heat transfer element (not shown in FIG. 5), as the blood moves forward during the systolic pulse, the first helical heat transfer segment 20 induces a counter-clockwise rotational inertia to the blood. As the blood reaches the second segment 22, the rotational direction of the inertia is reversed, causing turbulence within the blood. Further, as the blood reaches the third segment 24, the rotational direction of the inertia is again reversed. The sudden changes in flow direction actively reorient and randomize the velocity vectors, thus ensuring turbulence throughout the bloodstream. During turbulent flow, the velocity vectors of the blood become more random and, in some cases, become perpendicular to the axis of the artery. In addition, as the velocity of the blood within the artery decreases and reverses direction during the cardiac cycle, additional turbulence is induced and turbulent motion is sustained throughout the duration of each pulse through the same mechanisms described above.

Thus, a large portion of the volume of warm blood in the vessel is actively brought in contact with the heat transfer element 14, where it can be cooled by direct contact rather than being cooled largely by conduction through adjacent laminar layers of blood. As noted above, the depth of the grooves 26, 30, 34 (FIG. 2) is greater than the depth of the boundary layer which would develop if a straight-walled heat transfer element were introduced into the blood stream. In this way, free stream turbulence is induced. In the preferred embodiment, in order to create the desired level of turbulence in the entire blood stream during the whole cardiac cycle, the heat transfer element 14 creates a turbulence intensity greater than about 0.05. The turbulence intensity may be greater than 0.05, 0.06, 0.07 or up to 0.10 or 0.20 or greater.

Referring back to FIG. 2, the heat transfer element 14 has been designed to address all of the design criteria discussed above. First, the heat transfer element 14 is flexible and is made of a highly conductive material. The flexibility is provided by a segmental distribution of tube sections 25, 27 which provide an articulating mechanism. The tube sections have a predetermined thickness which provides sufficient flexibility. Second, the exterior surface area 37 has been increased through the use of helical ridges 28, 32, 36 and helical grooves 26, 30, 34. The ridges also allow the heat transfer element 14 to maintain a relatively atraumatic profile, thereby minimizing the possibility of damage to the vessel wall. Third, the heat transfer element 14 has been designed to promote turbulent kinetic energy both internally and externally. The modular or segmental design allows the direction of the invaginations to be reversed between segments. The alternating helical rotations create an alternating flow that results in mixing the blood in a manner analogous to the mixing action created by the rotor of a washing machine that switches directions back and forth. This mixing action is intended to promote high level turbulent kinetic energy to enhance the heat transfer rate. The alternating helical design also causes beneficial mixing, or turbulent kinetic energy, of the working fluid flowing internally.

Figure 6:
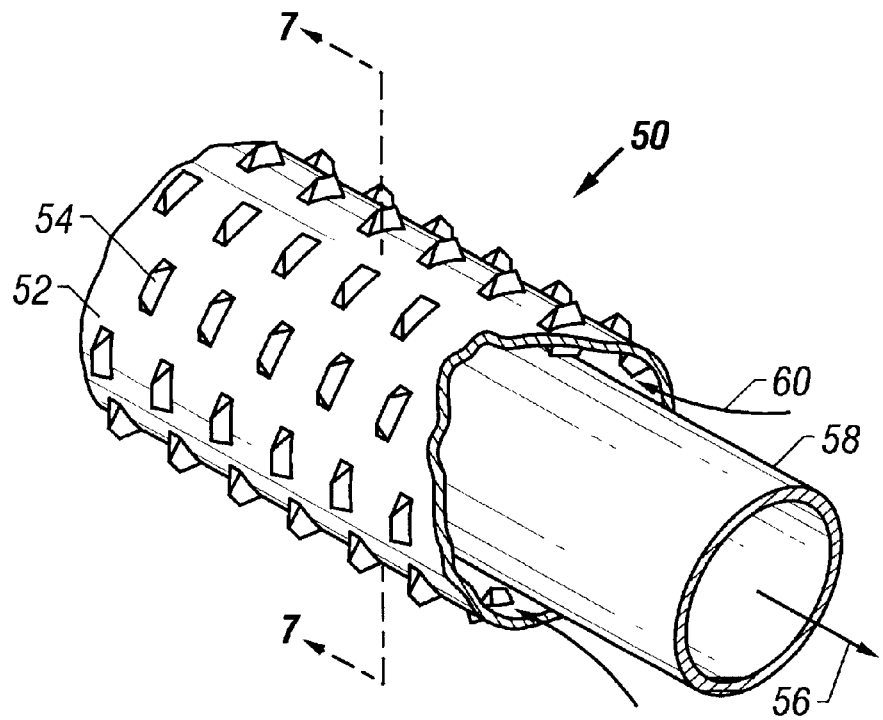
FIG. 6 is a cut-away perspective view of an alternative embodiment of a heat transfer element which may be employed according to the invention.

FIG. 6 is a cut-away perspective view of an alternative embodiment of a heat transfer element 50. An external surface 52 of the heat transfer element 50 is covered with a series of axially staggered protrusions 54. The staggered nature of the outer protrusions 54 is readily seen with reference to FIG. 7 which is a transverse cross-sectional view taken at a location denoted by the line 7—7 in FIG. 6. In order to induce free stream turbulence, the height, $d_p$, of the staggered outer protrusions 54 is greater than the thickness of the boundary layer which would develop if a smooth heat transfer element had been introduced into the blood stream. As the blood flows along the external surface 52, it collides with one of the staggered protrusions 54 and a turbulent wake flow is created behind the protrusion. As the blood divides and swirls along side of the first staggered protrusion 54, its turbulent wake encounters another staggered protrusion 54 within its path preventing the re-lamination of the flow and creating yet more turbulence. In this way, the velocity vectors are randomized and turbulence is created not only in the boundary layer but throughout the free stream. As is the case with the preferred embodiment, this geometry also induces a turbulent effect on the internal coolant flow.

Figure 7:
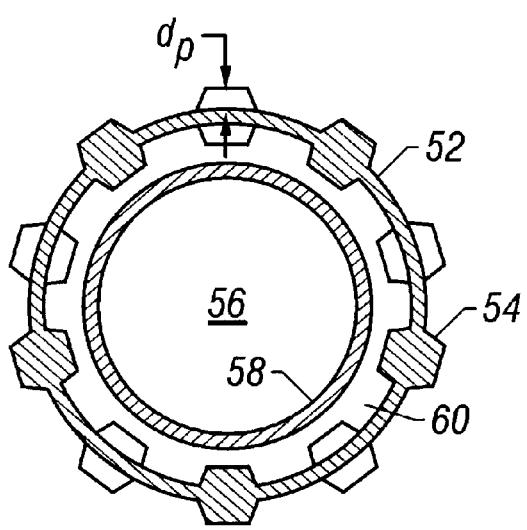
FIG. 7 is a transverse section view of the heat transfer element of FIG. 6.

A working fluid is circulated up through an inner coaxial lumen 56 defined by an insulating coaxial tube 58 to a distal tip of the heat transfer element 50. The working fluid then traverses an outer coaxial lumen 60 in order to transfer heat to the exterior surface 52 of the heat transfer element 50. The inside surface of the heat transfer element 50 is similar to the exterior surface 52, in order to induce turbulent flow of the working fluid. The inner protrusions can be aligned with the outer protrusions 54, as shown in FIG. 7, or they can be offset from the outer protrusions 54, as shown in FIG. 6.

Figure 8:
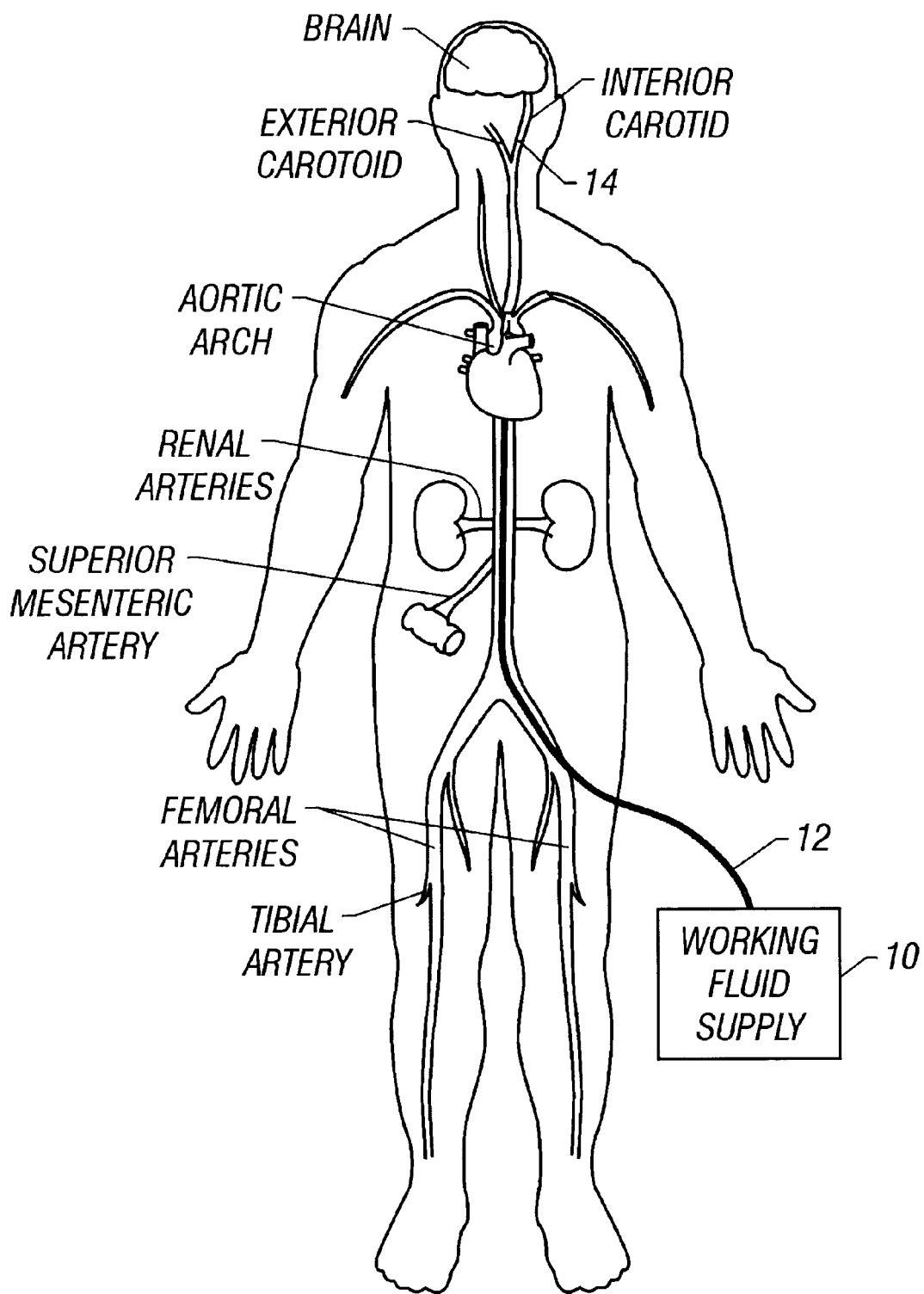
FIG. 8 is a schematic representation of the invention being used in one embodiment to cool the brain of a patient.

FIG. 8 is a schematic representation of the invention being used to cool the brain of a patient. The selective organ hypothermia apparatus shown in FIG. 8 includes a working fluid supply 10, preferably supplying a chilled liquid such as water, alcohol or a halogenated hydrocarbon, a supply catheter 12 and the heat transfer element 14. The supply catheter 12 has a coaxial construction. An inner coaxial lumen within the supply catheter 12 receives coolant from the working fluid supply 10. The coolant travels the length of the supply catheter 12 to the heat transfer element 14 which serves as the cooling tip of the catheter. At the distal end of the heat transfer element 14, the coolant exits the insulated interior lumen and traverses the length of the heat transfer element 14 in order to decrease the temperature of the heat transfer element 14. The coolant then traverses an outer lumen of the supply catheter 12 so that it may be disposed of or recirculated. The supply catheter 12 is a flexible catheter having a diameter sufficiently small to allow its distal end to be inserted percutaneously into an accessible artery such as the femoral artery of a patient as shown in FIG. 8. The supply catheter 12 is sufficiently long to allow the heat transfer element 14 at the distal end of the supply catheter 12 to be passed through the vascular system of the patient and placed in the internal carotid artery or other small artery. The method of inserting the catheter into the patient and routing the heat transfer element 14 into a selected artery is well known in the art.

Although the working fluid supply 10 is shown as an exemplary cooling device, other devices and working fluids may be used. For example, in order to provide cooling, freon, perflourocarbon, water, or saline may be used, as well as other such coolants.

The heat transfer element can absorb or provide over 75 Watts of heat to the blood stream and may absorb or provide as much as 100 Watts, 150 Watts, 170 Watts or more. For example, a heat transfer element with a diameter of 4 mm and a length of approximately 10 cm using ordinary saline solution chilled so that the surface temperature of the heat transfer element is approximately 5° C. and pressurized at 2 atmospheres can absorb about 100 Watts of energy from the bloodstream. Smaller geometry heat transfer elements may be developed for use with smaller organs which provide 60 Watts, 50 Watts, 25 Watts or less of heat transfer.

The practice of the present invention is illustrated in the following non-limiting example.

EXEMPLARY PROCEDURE

1. The patient is initially assessed, resuscitated, and stabilized.
2. The procedure is carried out in an angiography suite or surgical suite equipped with fluoroscopy.
3. Because the catheter is placed into the common carotid artery, it is important to determine the presence of stenotic atheromatous lesions. A carotid duplex (Doppler/ultrasound) scan can quickly and non-invasively make this determination. The ideal location for placement of the catheter is in the left carotid so this may be scanned first. If disease is present, then the right carotid artery can be assessed. This test can be used to detect the presence of proximal common carotid lesions by observing the slope of the systolic upstroke and the shape of the pulsation. Although these lesions are rare, they could inhibit the placement of the catheter. Examination of the peak blood flow velocities in the internal carotid can determine the presence of internal carotid artery lesions. Although the catheter is placed proximally to such lesions, the catheter may exacerbate the compromised blood flow created by these lesions. Peak systolic velocities greater that 130 cm/sec and peak diastolic velocities>100 cm/sec in the internal indicate the presence of at least 70% stenosis. Stenosis of 70% or more may warrant the placement of a stent to open up the internal artery diameter.
4. The ultrasound can also be used to determine the vessel diameter and the blood flow and the catheter with the appropriately sized heat transfer element could be selected.
5. After assessment of the arteries, the patients inguinal region is sterilely prepped and infiltrated with lidocaine.
6. The femoral artery is cannulated and a guide wire may be inserted to the desired carotid artery. Placement of the guide wire is confirmed with fluoroscopy.
7. An angiographic catheter can be fed over the wire and contrast media injected into the artery to further to assess the anatomy of the carotid.
8. Alternatively, the femoral artery is cannulated and a 10–12.5 french (f) introducer sheath is placed.
9. A guide catheter is placed into the desired common carotid artery. If a guiding catheter is placed, it can be used to deliver contrast media directly to further assess carotid anatomy.
10. A 10*f*–12*f* (3.3–4.0 mm) (approximate) cooling catheter is subsequently filled with saline and all air bubbles are removed.
11. The cooling catheter is placed into the carotid artery via the guiding catheter or over the guidewire. Placement is confirmed with fluoroscopy.
12. Alternatively, the cooling catheter tip is shaped (angled or curved approximately 45 degrees), and the cooling catheter shaft has sufficient pushability and torqueability to be placed in the carotid without the aid of a guide wire or guide catheter.
13. The cooling catheter is connected to a pump circuit also filled with saline and free from air bubbles. The pump circuit has a heat exchange section that is immersed into a water bath and tubing that is connected to a peristaltic pump. The water bath is chilled to approximately 0° C.
14. Cooling is initiated by starting the pump mechanism. The saline within the cooling catheter is circulated at 5 cc/sec. The saline travels through the heat exchanger in the chilled water bath and is cooled to approximately 1° C.
15. It subsequently enters the cooling catheter where it is delivered to the heat transfer element. The saline is warmed to approximately 5–7° C. as it travels along the inner lumen of the catheter shaft to the end of the heat transfer element.
16. The saline then flows back through the heat transfer element in contact with the inner metallic surface. The saline is further warmed in the heat transfer element to 12 –15° C., and in the process, heat is absorbed from the blood, cooling the blood to 30° C. to 32° C.
17. The chilled blood then goes on to chill the brain. It is estimated that 15–30 minutes will be required to cool the brain to 30 to 32° C.
18. The warmed saline travels back down the outer lumen of the catheter shaft and back to the chilled water bath where it is cooled to 1° C.
19. The pressure drops along the length of the circuit are estimated to be 2–3 atmospheres.
20. The cooling can be adjusted by increasing or decreasing the flow rate of the saline. Monitoring of the temperature drop of the saline along the heat transfer element will allow the flow to be adjusted to maintain the desired cooling effect.
21. The catheter is left in place to provide cooling for 12 to 24 hours.
22. If desired, warm saline can be circulated to promote warming of the brain at the end of the procedure.

Figure 9:
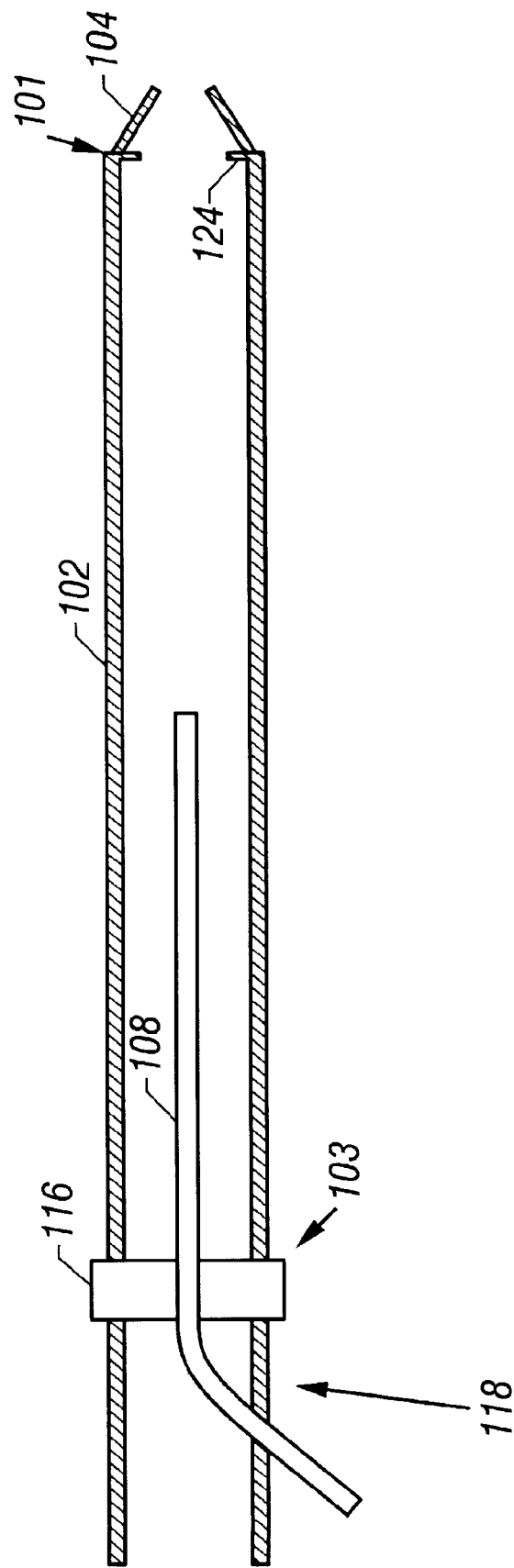
FIG. 9 is a cross-section of a guide catheter which may be employed for applications of the invention.

The invention may also be used in combination with other techniques. For example, one technique employed to place working lumens or catheters in desired locations employs guide catheters, as mentioned above. Referring to FIG. 9, a guide catheter 102 is shown which may be advantageously employed in the invention. The guide catheter 102 has a soft tapered tip 104 and a retaining flange 124 at a distal end 101.

The soft tapered tip 104 allows an atraumatic entrance of the guide catheter 102 into an artery as well as a sealing function as is described in more detail below. The retaining flange 124 may be a metallic member adhered to the guide catheter interior wall or may be integral with the material of the tube. The retaining flange 124 further has a sealing function described in more detail below.

The guide catheter 102 may have various shapes to facilitate placement into particular arteries. In the case of the carotid artery, the guide catheter 102 may have the shape of a hockey stick. The guide catheter 102 may include a Pebax® tube with a Teflon® liner. The Teflon® liner provides sufficient lubricity to allow minimum friction when components are pushed through the tube. A metal wire braid may also be employed between the Pebax® tube and the Teflon® liner to provide torqueability of the guide catheter 102.

A number of procedures may be performed with the guide catheter 102 in place within an artery. For example, a stent may be disposed across a stenotic lesion in the internal carotid artery. This procedure involves placing a guide wire through the guide catheter 102 and across the lesion. A balloon catheter loaded with a stent is then advanced along the guide wire. The stent is positioned across the lesion. The balloon is expanded with contrast, and the stent is deployed intravascularly to open up the stenotic lesion. The balloon catheter and the guide wire may then be removed from the guide catheter.

A variety of treatments may pass through the guide catheter. For example, the guide catheter, or an appropriate lumen disposed within, may be employed to transfer contrast for diagnosis of bleeding or arterial blockage, such as for angiography. The same may further be employed to deliver various drug therapies, e.g., to the brain. Such therapies may include delivery of thrombolytic drugs that lyse clots lodged in the arteries of the brain, as are further described in an application incorporated by reference above.

A proximal end 103 of the guide catheter 102 has a male luer connector for mating with a y-connector 118 attached to a supply tube 108. The supply tube 108 may include a braided Pebax® tube or a polyimide tube. The y-connector 118 connects to the guide catheter 102 via a male/female luer connector assembly 116. The y-connector 118 allows the supply tube 108 to enter the assembly and to pass through the male/female luer connector assembly 116 into the interior of the guide catheter 102. The supply tube 108 may be disposed with an outlet at its distal end. The outlet of the supply tube 108 may also be used to provide a working fluid to the interior of a heat transfer element 110. The guide catheter 102 may be employed as the return tube for the working fluid supply in this aspect of the invention. In this embodiment, a heat transfer element 110 is delivered to the distal end 101 of the guide catheter 102 as is shown in FIG. 10.

Figure 10:
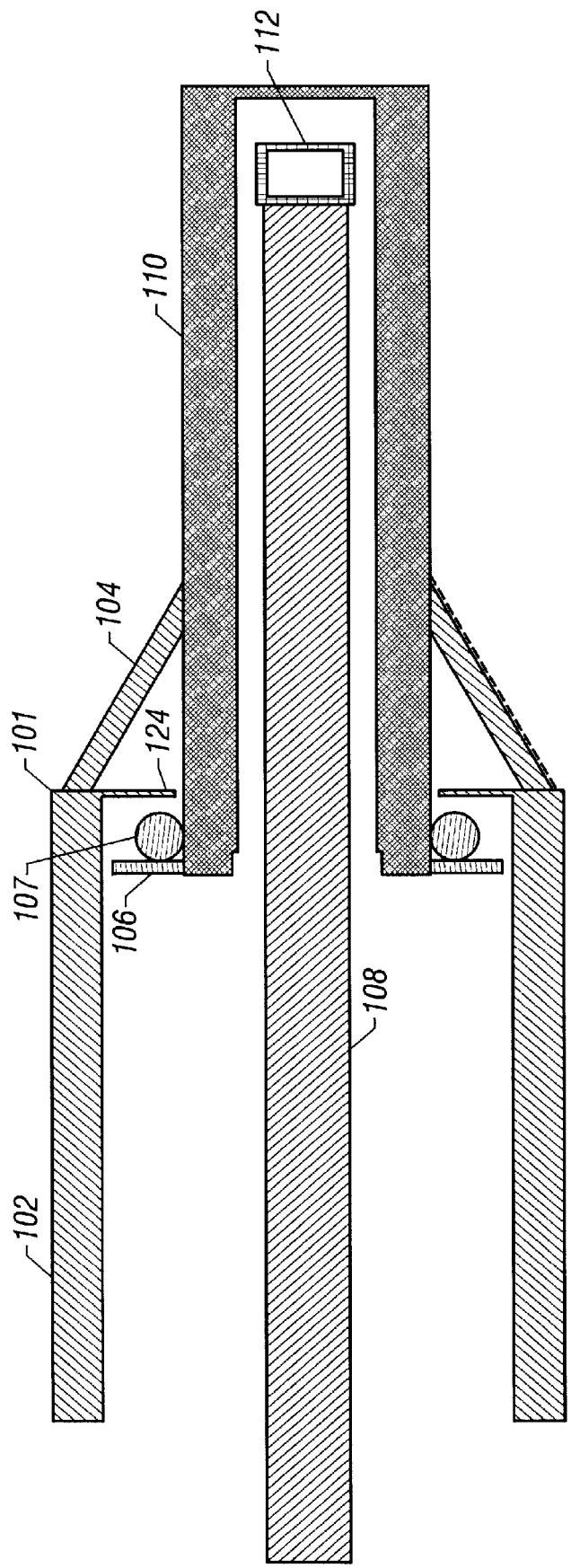
FIG. 10 is a schematic representation of the invention being used with a return tube/guide catheter.

In FIG. 10, the heat transfer element 110 is shown, nearly in a working location, in combination with the return tube/guide catheter 102. In particular, the heat transfer element 110 is shown near the distal end 101 of the return tube/guide catheter ("RTGC") 102. The heat transfer element 110 may be kept in place by a flange 106 on the heat transfer element 110 that abuts the retaining flange 124 on the RTGC 102. Flanges 124 and 106 may also employ o-rings such as an o-ring 107 shown adjacent to the flange 106. Other such sealing mechanisms or designs may also be used. In this way, the working fluid is prevented from leaking into the blood.

The supply tube 108 may connect to the heat transfer element 110 (the connection is not shown) and may be employed to push the heat transfer element 110 through the guide catheter 102. The supply tube should have sufficient rigidity to accomplish this function. In an alternative embodiment, a guide wire may be employed having sufficient rigidity to push both the supply tube 108 and the heat transfer element 110 through the guide catheter 102. So that the supply tube 108 is preventing from abutting its outlet against the interior of the heat transfer element 110 and thereby stopping the flow of working fluid, a strut 112 may be employed on a distal end of the supply tube 108. The strut 112 may have a window providing an alternative path for the flowing working fluid.

The heat transfer element 110 may employ any of the forms disclosed above, as well as variations of those forms. For example, the heat transfer element 110 may employ alternating helical ridges separated by flexible joints, the ridges creating sufficient turbulence to enhance heat transfer between a working fluid and blood in the artery. Alternatively, the heat transfer element 110 may be inflatable and may have sufficient surface area that the heat transfer due to conduction alone is sufficient to provide the requisite heat transfer. Details of the heat transfer element 110 are omitted in FIG. 10 for clarity.

Figure 11:
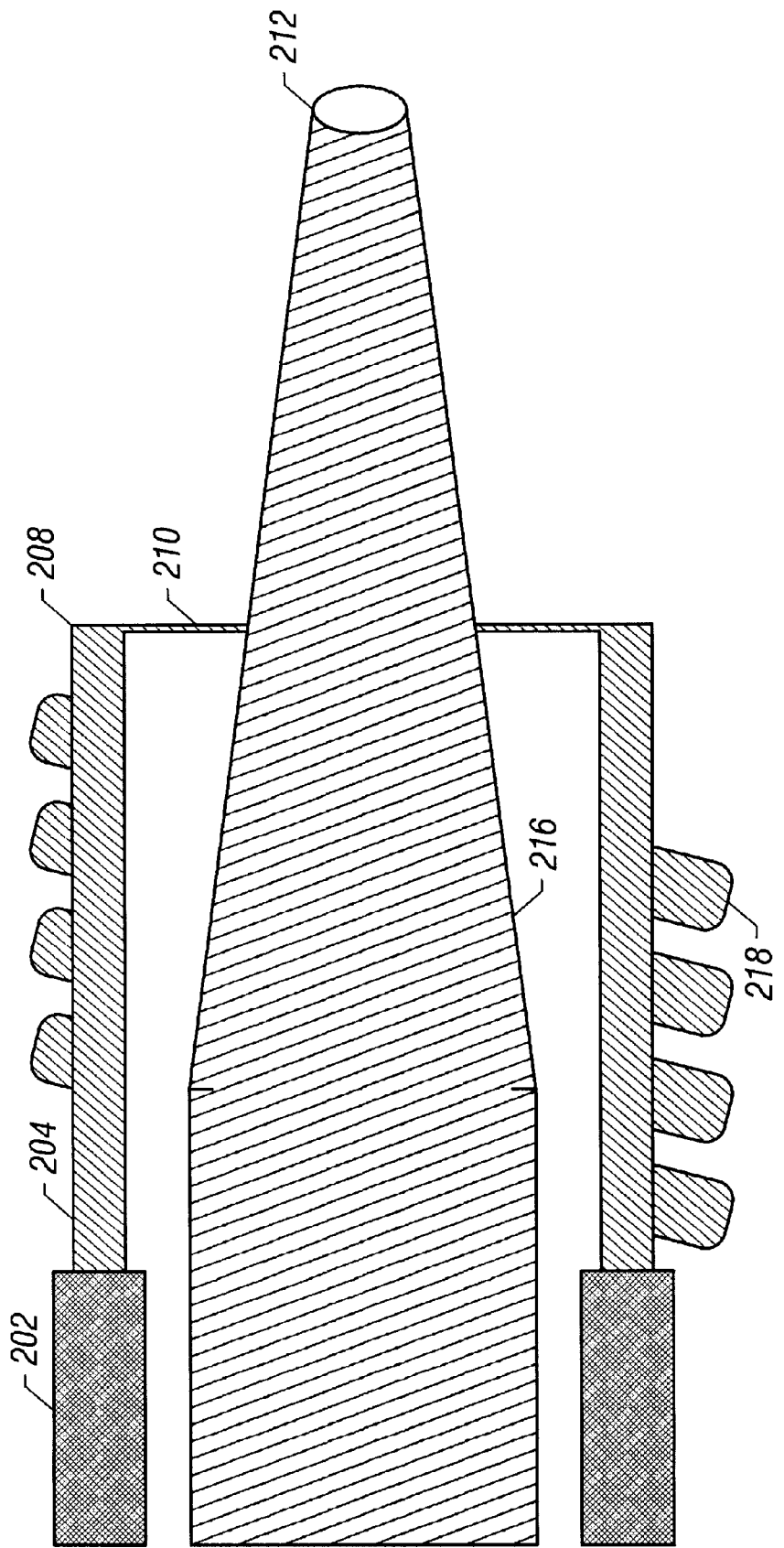
FIG. 11 is a schematic representation of the invention being used with a delivery catheter.

FIG. 11 shows an alternate embodiment of the invention in which a heat transfer element 204 employs an internal supply catheter 216. The heat transfer element 204 is shown with turbulence-inducing invaginations 218 located thereon. Similar invaginations may be located in the interior of the heat transfer element 204 but are not shown for clarity. Further, it should be noted that the heat transfer element 204 is shown with merely four invaginations. Other embodiments may employ multiple elements connected by flexible joints as is disclosed above. The single heat transfer element shown in FIG. 11 is provided merely for clarity.

A return supply catheter 202 is shown coupled to the heat transfer element 204. The return supply catheter may be coupled to the heat transfer element 204 in known fashion, and may provide a convenient return path for working fluid as may be provided to the heat transfer element 204 to provide temperature control of a flow or volume of blood.

A delivery catheter 216 is also shown in FIG. 11. The delivery catheter 216 may be coupled to a y-connector at its proximal end in the manner disclosed above. The delivery catheter 216 may be freely disposed within the interior of the return supply catheter 202 except where it is restrained from further longitudinal movement (in one direction) by a retaining flange 210 disposed at the distal end 208 of the heat transfer element 204. The delivery catheter 216 may be made sufficiently flexible to secure itself within retaining flange 210, at least for a short duration. The delivery catheter 216 may have a delivery outlet 212 at a distal end to allow delivery of a drug or other such material for therapeutic purposes. For example, a radioopaque fluid may be dispensed for angiography or a thrombolytic drug for thrombinolysis applications.

For applications in which it is desired to provide drainage of the artery, e.g., laser ablation, the delivery catheter may be pulled upstream of the retaining flange 210, exposing an annular hole in fluid communication with the return supply catheter 202. The return supply catheter 202 may then be used to drain the volume adjacent the retaining flange 210.

Figure 12:
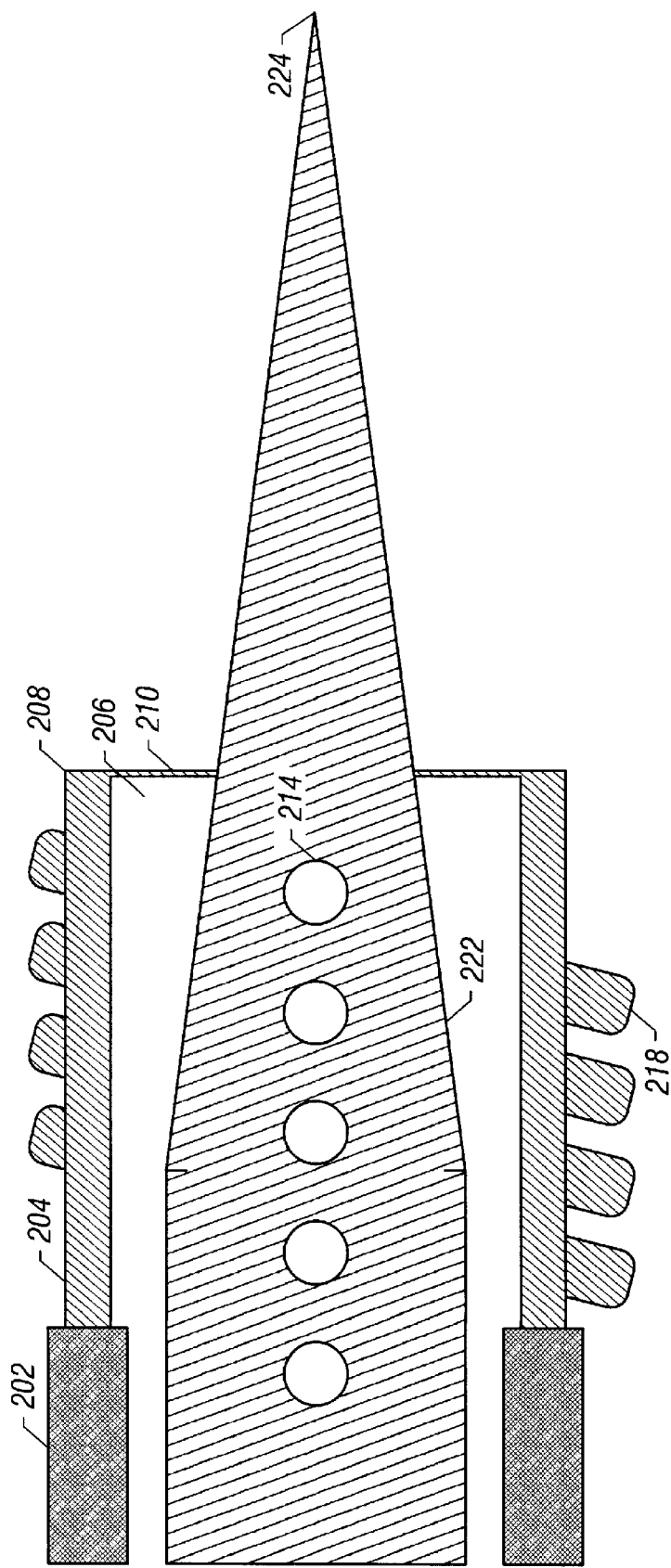
FIG. 12 is a schematic representation of the invention being used with a working fluid catheter.

The assembly may also perform temperature control of blood in the artery where the same is located. Such temperature control procedures may be performed, e.g., before or after procedures involving the delivery catheter 216. Such a device for temperature control is shown in FIG. 12. In this figure, a working fluid catheter 222 is disposed within the return supply catheter 202 and the heat transfer element 204. In a manner similar to the delivery catheter 216, the working fluid catheter may be freely disposed within the interior of the return supply catheter 202 and may further be coupled to a y-connector at its proximal end in the manner disclosed above. The working fluid catheter 222 may further be made sufficiently flexible to secure itself within retaining flange 210, at least for a short duration. The working fluid catheter 222 may have a plurality of outlets 214 to allow delivery of a working fluid. The outlets 214 are located near the distal end 224 of the working fluid catheter 222 but somewhat upstream. In this way, the outlets 214 allow dispensation of a working fluid into the interior of the heat transfer element 204 rather than into the blood stream. The working fluid catheter 222 may also be insulated to allow the working fluid to maintain a desired temperature without undue heat losses to the walls of the working fluid catheter 222.

Figure 14:
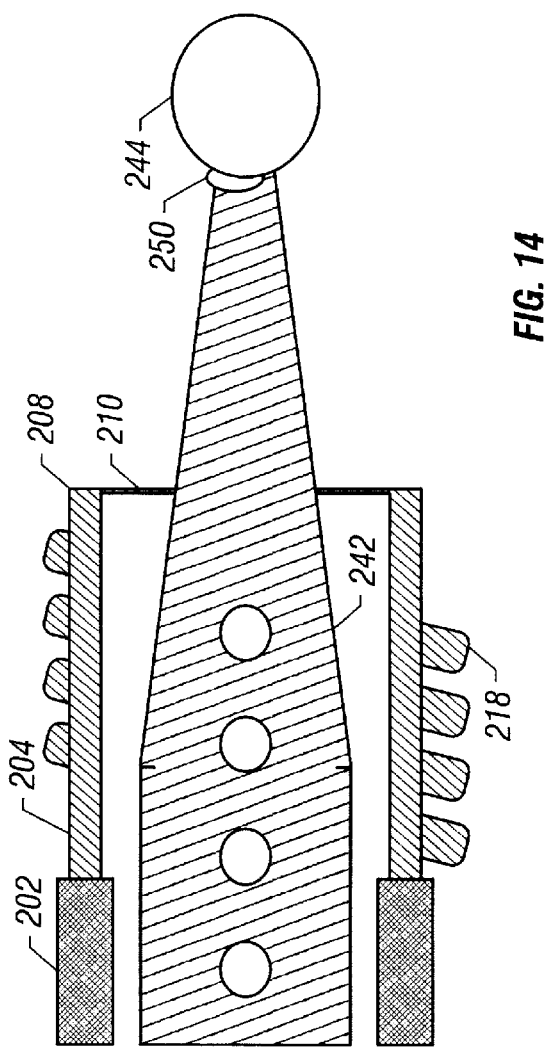
FIG. 14 is a schematic representation of the invention being used with a delivery/working fluid catheter with a balloon attachment.
Figure 15:
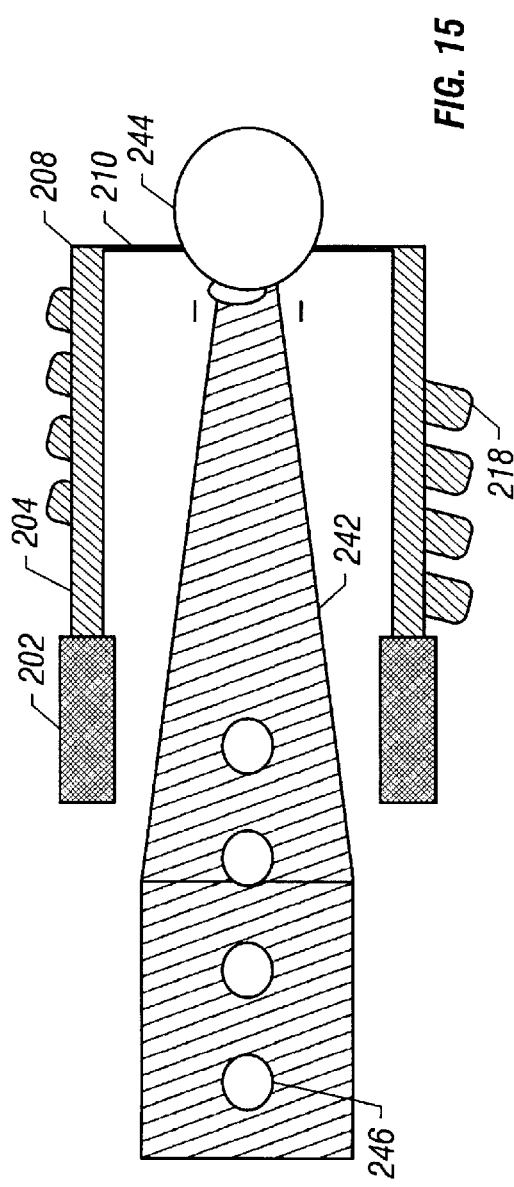
FIG. 15 is a second schematic representation of the invention being used with a delivery/working fluid catheter with a balloon attachment.

One way of using the same catheter as a delivery catheter and as a working fluid catheter is shown in FIGS. 14 and 15. In FIG. 14, a delivery/working fluid catheter 248 is shown in a position similar to the respective catheters of FIGS. 11 and 12. The delivery/working fluid catheter 248 has working fluid outlets and a delivery outlet, and is further equipped with a balloon 244 disposed at the distal end. Balloon 244 may be inflated with a separate lumen (not shown). By retracting the delivery/working fluid catheter 248 to the position shown in FIG. 15, the balloon 244 may be made to seal the hole defined by retaining flange 210, thereby creating a fluid-tight seal so that working fluid may be dispensed from outlets 246 to heat or cool the heat transfer element 204.

Figure 13:
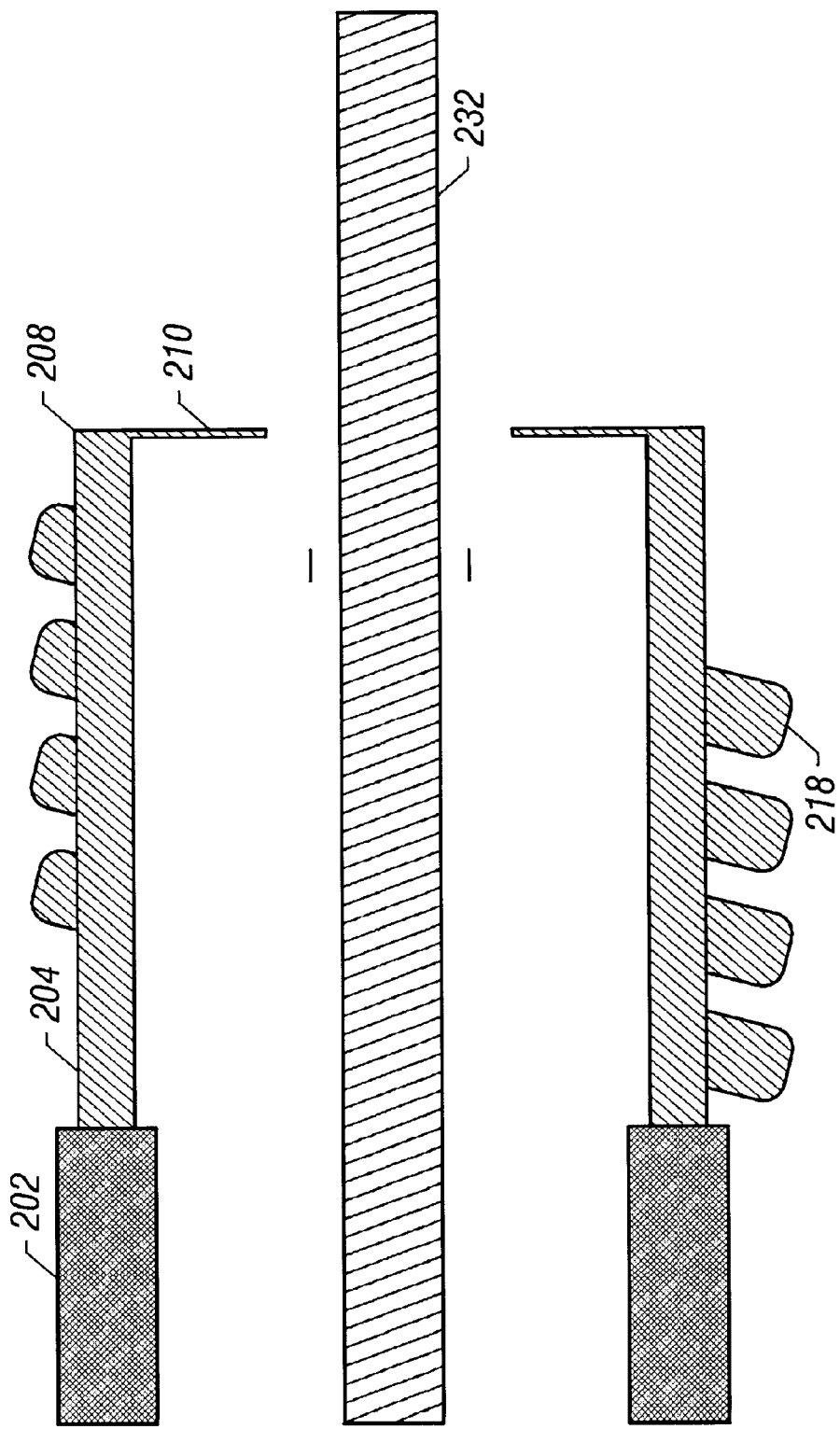
FIG. 13 is a schematic representation of the invention being used with a guide wire.

One method of disposing a heat transfer device within a desired artery, such as the carotid artery, involves use of a guide wire. Referring to FIG. 13, a guide wire 232 is shown disposed within the interior of the heat transfer element 204. The heat transfer element 204 may conveniently use the hole defined by retaining flange 210 to be threaded onto the guide wire 232.

Numerous other therapies may then employ the return supply catheter and heat transfer element as a "guide catheter". For example, various laser and ultrasound ablation catheters may be disposed within. In this way, these therapeutic techniques may be employed at nearly the same time as therapeutic temperature control, including, e.g., neuroprotective cooling.

The invention has also been described with respect to certain embodiments. It will be clear to one of skill in the art that variations of the embodiments may be employed in the method of the invention. Accordingly, the invention is limited only by the scope of the appended claims.

What is claimed is:

1. A method for performing stenting of a stenotic lesion during selective vessel hypothermia, comprising:

introducing a guide catheter into a blood vessel;

introducing a guide wire through the guide catheter and across a stenotic lesion;

delivering a balloon catheter loaded with a stent via the guide wire;

positioning the stent across the lesion;

expanding the balloon;

deploying the stent;

introducing a supply tube having a transfer element at a distal end thereof into the blood vessel through the guide catheter; and cooling the heat transfer element, by flowing a working fluid through the heat transfer element,
wherein the heat transfer element is not used to deploy the stent, and
further wherein blood in the blood vessel is cooled to a prespecified temperature range by flowing past the heat transfer element.

2. The method of claim 1, wherein the heat element has a plurality of exterior surface irregularities, the surface irregularities having a depth greater than the boundary layer thickness of flow in the blood vessel.

3. The method of claim 2, further comprising the step of:

creating turbulence around the surface irregularities at a distance from the heat transfer element greater than the boundary layer thickness of flow in the blood vessel, thereby creating turbulence throughout the blood flow in the blood vessel.

4. The method of claim 3, wherein:

the surface irregularities on the heat transfer element comprise a plurality of segments of helical ridges and grooves having alternating directions of helical rotation; and turbulence is created by establishing repetitively alternating directions of helical blood flow with the alternating helical rotations of the ridges and grooves.

5. The method of claim 1, wherein the step of introducing a supply tube having a heat transfer element occurs at or near the same time as the step of deploying the stent.

6. The method of claim 1, wherein the step of introducing a supply tube having a heat transfer element occurs after the step of deploying the stent.

* * * * *